(12) United States Patent
Amin et al.

(10) Patent No.: US 10,844,003 B1
(45) Date of Patent: Nov. 24, 2020

(54) DUAL PPAR-DELTA AND PPAR-GAMMA AGONISTS

(71) Applicants: Auburn University, Auburn, AL (US); Ferris State University, Big Rapids, MI (US)

(72) Inventors: Rajesh H. Amin, Waverly, AL (US); Tracey Ward, Rockford, MI (US)

(73) Assignees: Auburn University, Auburn, AL (US); Ferris State University, Big Rapids, MI (US)

( * ) Notice: Subject to any disclaimer, the term of this patent is extended or adjusted under 35 U.S.C. 154(b) by 0 days.

(21) Appl. No.: 16/108,511

(22) Filed: Aug. 22, 2018

Related U.S. Application Data

(60) Provisional application No. 62/548,617, filed on Aug. 22, 2017.

(51) Int. Cl.
*C07C 229/38* (2006.01)
*A61P 3/10* (2006.01)
*A61P 25/28* (2006.01)

(52) U.S. Cl.
CPC .............. *C07C 229/38* (2013.01); *A61P 3/10* (2018.01); *A61P 25/28* (2018.01)

(58) Field of Classification Search
None
See application file for complete search history.

(56) References Cited

U.S. PATENT DOCUMENTS 9,422,239 B1 * 8/2016 Amin .................. C07D 209/48

OTHER PUBLICATIONS

Gathiaka et al. Design, development and evaluation of novel dual PPARdelta/PPARgamma agonists. Bioorganic & Medicinal Chemistry Letters, 23, 2013, 873-879.*
Artis, Dean R., et al. "Scaffold-based discovery of indeglitazar, a PPAR pan-active anti-diabetic agent." Proceedings of the National Academy of Sciences 106.1 (2009): 262-267.
Lewis, Stephanie N., Josep Bassaganya-Riera, and David R. Bevan. "Virtual screening as a technique for PPAR modulator discovery." PPAR research 2010 (2009) 11 pages.
Connors, Richard V., et al. "Identification of a PPARδ agonist with partial agonistic activity on PPARγ." Bioorganic & medicinal chemistry letters 19.13 (2009): 3550-3554.
Gathiaka et al., "Design, development and evaluation of novel dual PPARdelta/PPARgamma agonists," Bioorg Med Chem Lett., 2013; 23(3):873-879.
S.M. Berge, et al., "Pharmaceutical Salts," Journal of Pharmaceutical Sciences, vol. 66, No. 1, Jan. 1977 (19 pages).
P. Stahl, et al., Handbook of Pharmaceutical Salts: Properties, Selection and Use, (VCHA/Wiley-VCH, 2002) (book reference, not submitted—Applicants will provide a copy if requested).

* cited by examiner

*Primary Examiner* — Anna Pagonakis
(74) *Attorney, Agent, or Firm* — Riverside Law LLP

(57) ABSTRACT

The present invention relates to compositions and methods using for activating Peroxisomal Proliferator Activating Receptor (PPAR)-β/δ and/or PPAR-γ. In some embodiments, the present invention relates to compounds and methods of treating a disease or disorder associated with PPAR-β/δ and/or PPAR-γ. In some embodiments, present invention relates to compounds and methods of treating Alzheimer's disease, diabetes, and reduced cognition.

3 Claims, 38 Drawing Sheets

DUAL PPAR-DELTA AND PPAR-GAMMA AGONISTS

CROSS-REFERENCE TO RELATED APPLICATIONS

The present invention is entitled to priority to U.S. Provisional Application No. 62/548,617, filed Aug. 22, 2017, which is incorporated by reference herein in its entirety.

BACKGROUND OF THE INVENTION

Currently, the prevalence of diabetes mellitus is at an epidemic proportion in the general population and is associated with excessive cardiovascular morbidity and mortality. In particular, both impaired insulin secretion and resistance contribute to the development of the disease, particularly Type 2 diabetes mellitus. The drug class known as thiazolidinediones (TZDs) has been shown to improve whole body insulin sensitivity. The beneficial effects of TZDs are attributed to the activation of the nuclear receptor class of transcription factors known as PPAR (Peroxisomal Proliferator Activating Receptor). The PPAR family of nuclear receptors includes three members (PPARα, PPARβ/δ, and PPARγ) that are highly conserved in mammals, each forming a functional heterodimeric complex with 9-cis retinoic acid receptor (RXR).

However, currently available TZDs are associated with adverse cardiovascular events mostly due to development of peripheral edema and weight gain. For example, a full PPARγ agonist (rosiglitazone) has been shown to increase the risk of adverse cardiovascular events, in part due to the increase in fluid retention. Rosiglitazone is known to bind in the ligand binding domain (AF2 domain) of the PPAR-gamma receptor. This ligand interacts with many amino acids that confer bioactivity, especially His 449 and Tyr 443. It has been determined that Tyr 473 induces the increase in adipocyte maturation, including lipid accumulation and storage. However, strong interaction with this site also has led to unwanted off target effects including increased sodium retention in the kidneys, increased edema, ectopic fat accumulation in the heart, liver and muscle including skeletal muscle and heart. Therefore, the full agonist activity at PPARγ is believed to be associated with the deleterious side effects observed following treatment with TZDs such as rosiglitazone and pioglitazone.

PPARβ/δ activation is associated with improving overall circulating cholesterol levels (HDL, LDL, and triglycerides) and is ubiquitously expressed throughout the body. Furthermore, overexpression of PPARβ/δ in skeletal muscle improves the glycolytic muscle fiber type in animal models and thus improves circulating glucose and fatty acid levels. However, agonists for this class of receptors do not have a significant impact upon improving insulin sensitivity.

Therefore, there exists a need for new compounds that can effectively treat diabetes mellitus. Because diabetes and metabolic syndrome are associated with defects in glucose oxidation and lipid metabolism, the development of dual agonists that can activate both PPARβ/δ and PPARγ simultaneously is highly desirable.

Furthermore, Alzheimer's disease (AD) is one the fifth leading causes of death amongst people over 65 years and over in the United States, illustrating the limitations of the current therapies to prevent the progression of the disease. Continuous increase in the mortality rates due to AD indicates the critical need for new drug discovery based upon discovery of novel molecular targets for therapeutic potential. In particular, possible novel molecular targets correlations between Type 2 diabetes mellitus and AD have been found to have direct pathological links. Moreover, the epidemic proportions of Type 2 diabetes mellitus highlights the contribution of diabetes to the development of AD. Although there are direct links between AD and diabetes in the manifestation of cognitive impairment, there is a lack of vital knowledge to understanding how impaired insulin signaling directly alters memory in AD.

It is well known that PPARs are centrally involved in regulating whole body insulin sensitivity and may serve as a potential therapeutic target for AD. Pharmacological activation of PPARs has been shown to improve pathologies as well as learning and memory in transgenic AD animal models. However, there exists a need to provide insights into the molecular signaling mechanisms mediated by central (hippocampal) PPAR activation and improved cognition in AD.

Recently, ligand based activation of the nuclear receptor PPARγ has been shown to improve cognition in AD patients and transgenic animal models of AD by attenuating amyloid beta levels and Tau hyperphosphorylation. However, the use of TZDs for AD is limited due to their poor blood-brain barrier (BBB) permeability and undesirable side effects. Pioglitazone (a PPARγ agonist) and rosiglitazone (a full PPARγ agonist) were initially characterized as BBB impermeable, thus requiring high dose treatment over an extended period of time to obtain a significant therapeutic effect. However, long term treatment of high doses of rosiglitazone lead to life threatening side effects in humans.

Thus, there remains a need in the art for compounds with activity as PPARβ/δ and PPARγ dual agonists. Further, there is a need for therapies to treat diabetes mellitus and Alzheimer's disease. The present invention addresses this unmet need.

SUMMARY OF THE INVENTION

In one aspect, the present invention provides compounds represented by formula (1):

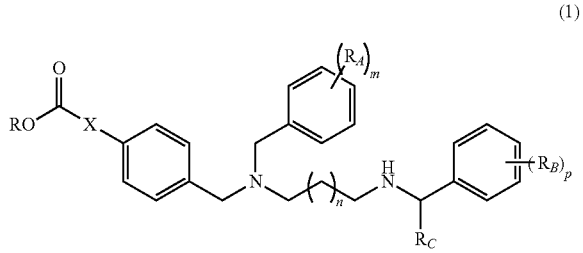

wherein,

X is selected from the group consisting of a single bond or $CR_1R_2$;

R is selected from the group consisting of hydrogen, $C_1$-$C_6$ alkyl, halogen, CN, $CF_3$, aryl, heteroaryl, cycloalkyl, and heterocyclyl;

n is an integer from 1 to 3;

m is an integer from 1 to 5;

p is an integer from 1 to 5;

each occurrence of $R_A$ is independently selected from the group consisting of hydrogen, F, and $CF_3$;

each occurrence of $R_B$ is independently selected from the group consisting of hydrogen, $C_1$-$C_6$ alkyl, halogen, CN, CF$_3$, aryl, heteroaryl, cycloalkyl, heterocyclyl, a substituted heteroaryl, and a substituted aryl;

R$_C$ is selected from the group consisting of hydrogen, C$_1$-C$_6$ alkyl, aryl, and heteroaryl; and R$_1$ and R$_2$ are each independently selected from the group consisting of hydrogen, C$_1$-C$_6$ alkyl, halogen, CN, CF$_3$, aryl, heteroaryl, cycloalkyl, heterocyclyl, a substituted heteroaryl, and a substituted aryl.

In one embodiment, X is selected from the group consisting of a single bond, —CH$_2$—, and —CH(CH$_3$)—.

In one embodiment, R is hydrogen.

In one embodiment, n is 1.

In one embodiment, m is 2 and each occurrence of R$_A$ is CF$_3$.

In one embodiment, each occurrence of R$_B$ is selected from the group consisting of hydrogen, methyl, t-butyl, isopropyl, and phenyl.

In one embodiment, p is 2.

In one embodiment, R$_C$ is selected from the group consisting of H and phenyl.

In one embodiment, the compound is selected from the group consisting of

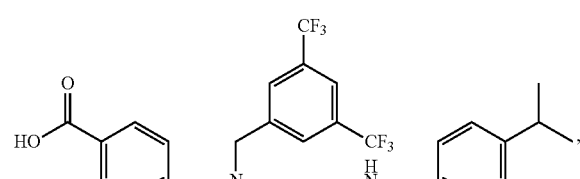
,
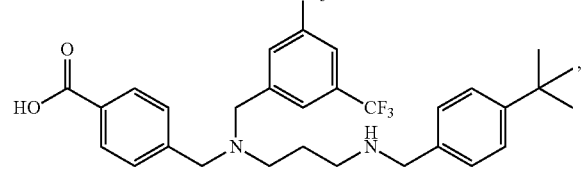
,
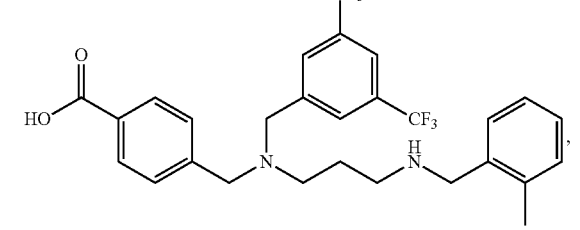
,
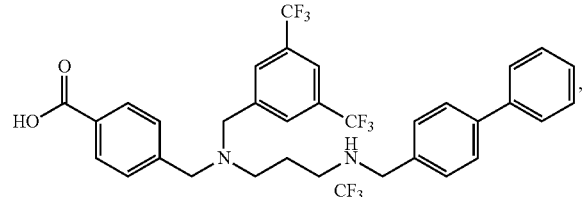
,
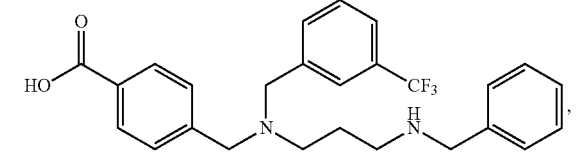
,
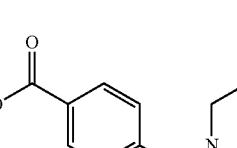
,
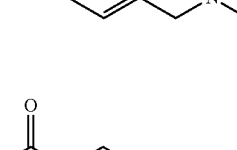
, and

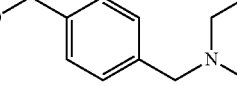
.

In one embodiment, the invention provides a composition comprising a compound of formula (1). In one embodiment, the composition further comprises an additional therapeutic.

In one aspect, the invention provides a method for activating Peroxisomal Proliferator Activating Receptor (PPAR)-β/δ and/or PPAR-γ in a subject in need thereof. In one embodiment, the method comprises administering to the subject a compound represented by formula (1). In one embodiment, PPAR-γ is partially activated.

In one aspect, the invention provides for treating or a disease or disorder associated with Peroxisomal Proliferator Activating Receptor (PPAR)-β/δ and/or PPAR-γ in a subject in need thereof. In one embodiment, the method comprises administering to the subject a compound represented by formula (1). In one embodiment, the disease or disorder associated with PPAR-β/δ and/or PPAR-γ is selected from the group consisting of Alzheimer's disease, diabetes, and reduced cognition.

BRIEF DESCRIPTION OF THE DRAWINGS

The following detailed description of the embodiments of the invention will be better understood when read in conjunction with the appended drawings. It should be understood, however, that the invention is not limited to the precise arrangements and instrumentalities of the embodiments shown in the drawings.

DETAILED DESCRIPTION

Figure 1:
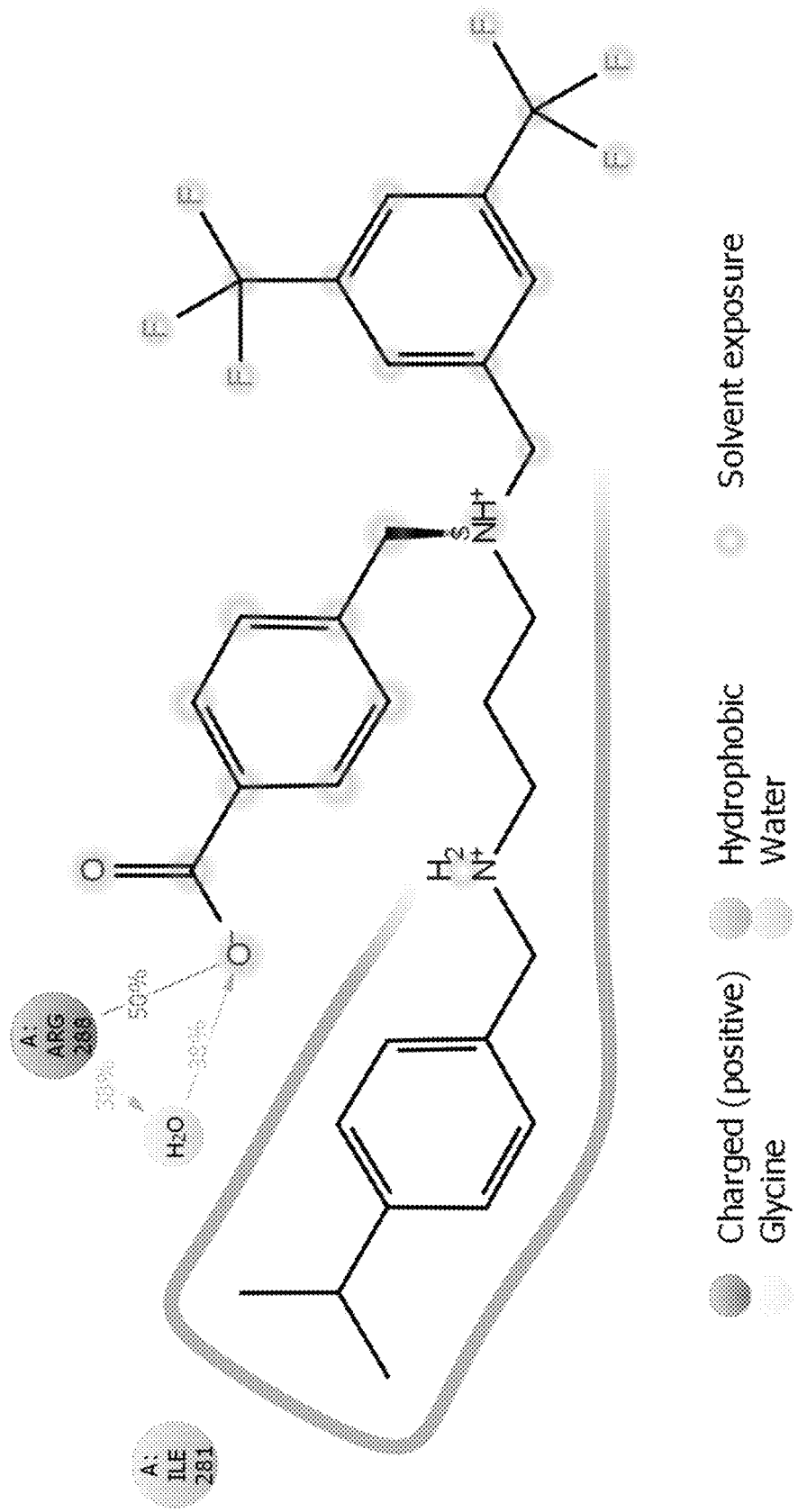
FIG. 1 is a schematic of detailed ligand atom interactions for compound AU9-1 with the PPARγ residues, derived from a 100 ns molecular dynamics (MD) simulation. Interactions that occur more than 30.0% of the simulation time in the selected trajectory (0.00 through 100.00 nsec), are shown.

The present invention relates to compositions and methods using for activating Peroxisomal Proliferator Activating Receptor (PPAR)-β/δ and/or PPAR-γ. For example, in certain embodiments the present invention relates to compounds and methods for treating a disease or disorder associated with PPAR-β/δ and/or PPAR-γ. In some embodiments, the compounds and methods of the invention are useful for treating diabetes mellitus and Alzheimer's disease.

Definitions

Unless defined otherwise, all technical and scientific terms used herein have the same meaning as commonly understood by one of ordinary skill in the art to which this invention belongs. The skilled artisan will understand that any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs or symptoms of pathology disease or disorder, for the purpose of diminishing or eliminating those signs or symptoms.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell from a patient (e.g., for diagnosis or ex vivo applications), who has a disease or disorder contemplated herein, a sign or symptom of a disease or disorder contemplated herein or the potential to develop a disease or disorder contemplated herein, with the purpose to cure, heal, alleviate, relieve, alter, remedy, ameliorate, improve or affect a disease or disorder contemplated herein, the signs or symptoms of a disease or disorder contemplated herein or the potential to develop a disease or disorder contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a sufficient amount of an agent to provide the desired biological or physiologic result. That result may be reduction and/or alleviation of a sign, a symptom, or a cause of a disease or disorder, or any other desired alteration of a biological system. An appropriate effective amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "potency" refers to the dose needed to produce half the maximal response ($ED_{50}$).

As used herein, the term "efficacy" refers to the maximal effect (Eurax) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —$NH_2$, amino, azido, —$N(CH_3)_2$, —C(=O)OH, trifluoromethyl, —C(=O)O($C_1$-$C_4$)alkyl, —C(=O)$NH_2$, —$SO_2NH_2$, —C(=NH)$NH_2$, and —$NO_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$-0H, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms.

Illustrative examples of cycloalkyl groups include, but are not limited to, the following moieties:

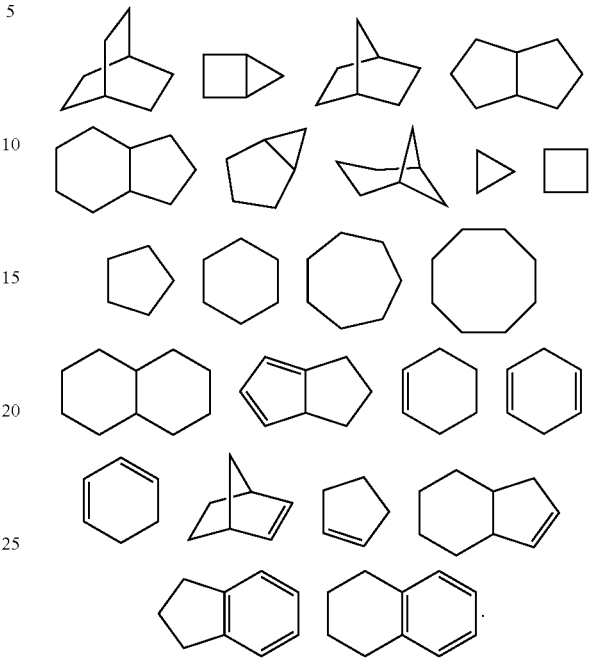

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from 0, S and N. In one embodiment, each heterocycloalkyl group has from 4 to 10 atoms in its ring system, with the proviso that the ring of said group does not contain two adjacent 0 or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

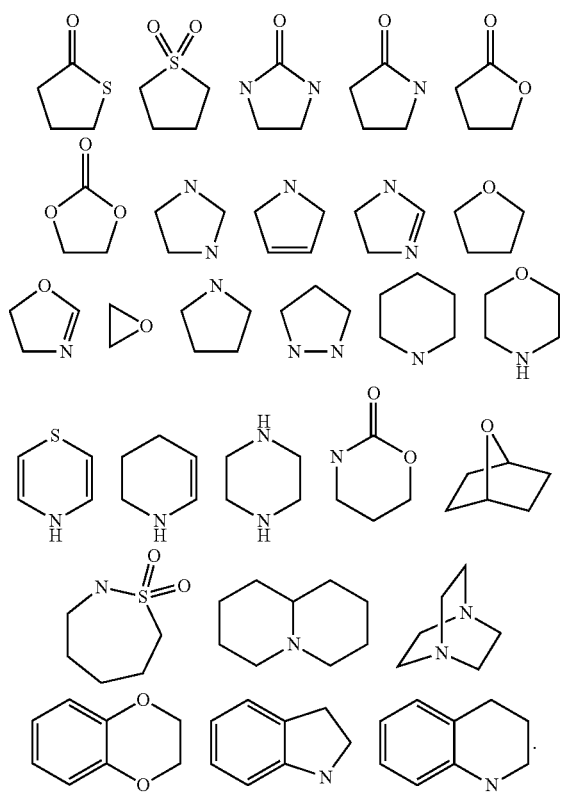

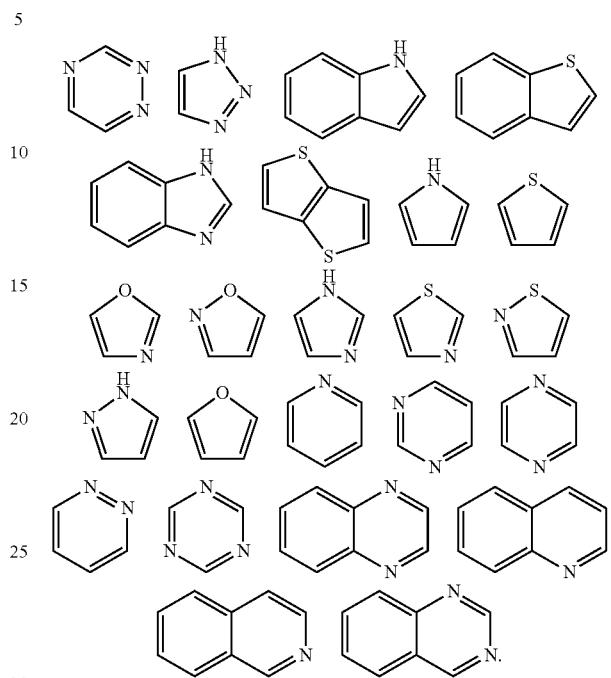

cyclic heteroaryl may include one or more rings that are partially saturated. Examples include the following moieties:

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. In one embodiment, aryl-($C_1$-$C_3$)alkyl is aryl-$CH_2$— or aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]2, and —C(NH$_2$)[substituted or unsubstituted alkyl]2. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (1), or a pharmaceutically acceptable salt, solvate, hydrate or stereoisomer thereof:

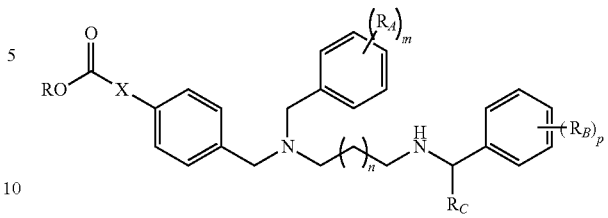

(1)

wherein,

X is selected from the group consisting of a single bond or CR$_1$R$_2$;

R is selected from the group consisting of hydrogen, C$_1$-C$_6$ alkyl, halogen, CN, CF$_3$, aryl, heteroaryl, cycloalkyl, and heterocyclyl;

n is an integer from 1 to 3;

m is an integer from 1 to 5;

p is an integer from 1 to 5;

each occurrence of R$_A$ is independently selected from the group consisting of hydrogen, F, and CF$_3$;

each occurrence of R$_B$ is independently selected from the group consisting of hydrogen, C$_1$-C$_6$ alkyl, halogen, CN, CF$_3$, aryl, heteroaryl, cycloalkyl, heterocyclyl, a substituted heteroaryl, and a substituted aryl;

R$_C$ is selected from the group consisting of hydrogen, C$_1$-C$_6$ alkyl, aryl, and heteroaryl; and R$_1$ and R$_2$ are each independently selected from the group consisting of hydrogen, C$_1$-C$_6$ alkyl, halogen, CN, CF$_3$, aryl, heteroaryl, cycloalkyl, heterocyclyl, a substituted heteroaryl, and a substituted aryl.

In one embodiment, X is selected from the group consisting of a single bond, —CH$_2$—, and —CH(CH$_3$)—.

In one embodiment, R is hydrogen.

In one embodiment, n is 1.

In one embodiment, m is 2 and each occurrence of R$_A$ is CF$_3$.

In one embodiment, each occurrence of R$_B$ is selected from the group consisting of hydrogen, methyl, t-butyl, isopropyl, and phenyl.

In one embodiment, p is 2. In one embodiment, p is 2 and each occurrence of R$_B$ is methyl. In one embodiment, p is 2, 3, 4, or 5. In one embodiment, p is not 1.

In one embodiment, wherein R$_C$ is selected from the group consisting of H and phenyl.

In one embodiment, when R$_B$ is methyl, and p is 1, the methyl is not in the para position. In one embodiment, when p is 1, R$_B$ is not in the para position.

In one embodiment, R$_B$ is selected from the group consisting of:

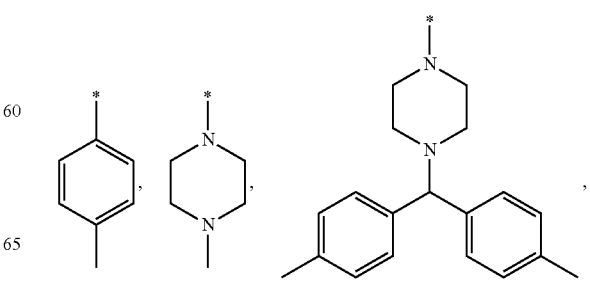

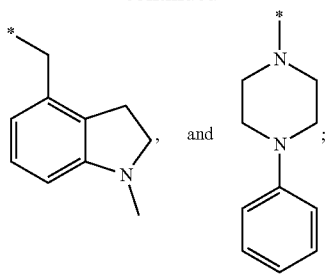

wherein * represents the binding location.

In one embodiment, $R_1$ and $R_2$ are each independently selected from the group consisting of hydrogen and methyl. In one embodiment, $R_1$ and $R_2$ are each hydrogen. In one embodiment, $R_1$ and $R_2$ are each methyl.

In one embodiment, the compound of formula (1) is selected from

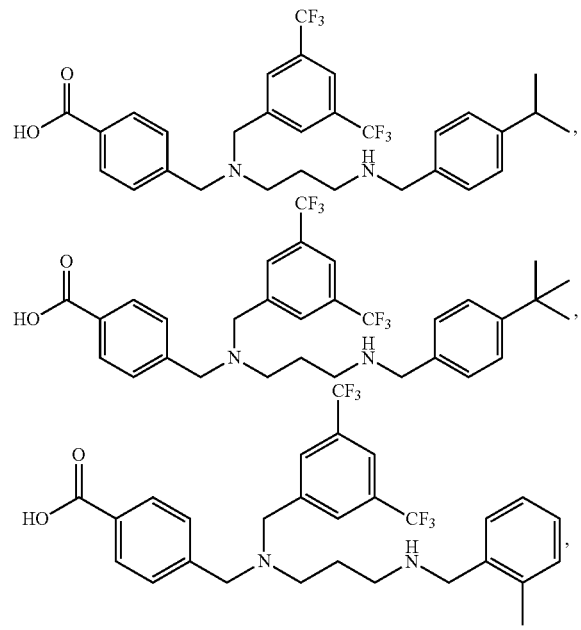

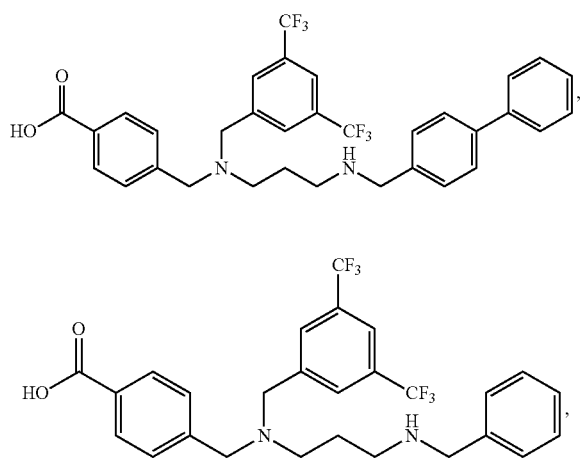

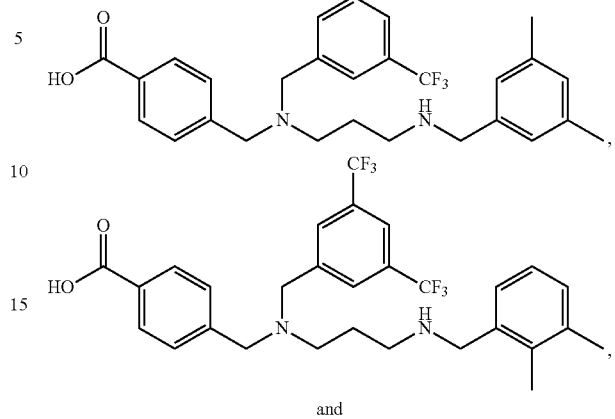

and

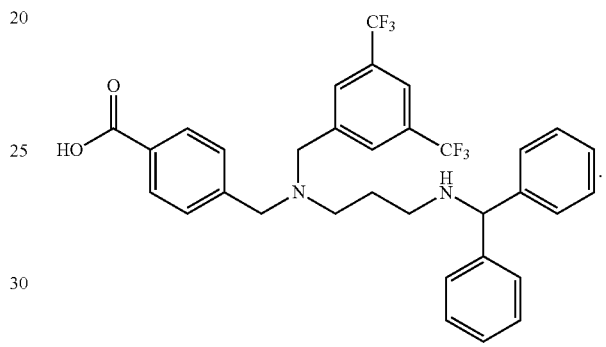

Compounds of the invention may be prepared by the general schemes described herein, using the synthetic method known by those skilled in the art.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference in their entirety). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with, for example, Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

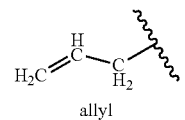
allyl

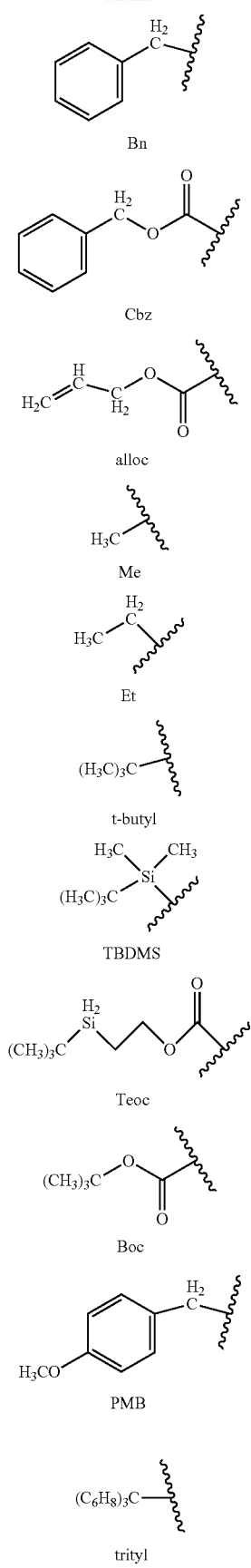

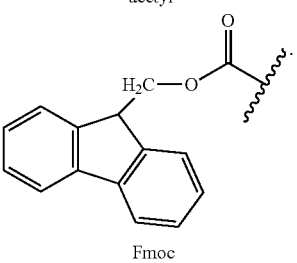

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods

In some embodiments, the invention provides methods of activating Peroxisomal Proliferator Activating Receptor (PPAR)-β/δ and/or PPAR-γ in a subject in need thereof. In one embodiment, the method comprises administering to the subject an effective amount of a composition comprising a compound of the invention.

In one embodiment, the invention provides a method of partially activating PPAR-γ. For example, in one embodiment the method activates β/δ and/or PPAR-γ about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%.

In some aspects, the partial PPAR-γ agonists have reduced cardiac toxicity compared to full PPAR-γ agonists. Thus, in one embodiment, the methods of the invention have reduced cardiac toxicity. In some aspects, the partial PPAR-γ agonists have increased brain localization compared to full PPAR-γ agonists. Thus, in one embodiment, the methods of the invention have enhanced brain localization.

In one embodiment, the invention provides a method for treating or preventing a disease or disorder associated with PPAR-β/δ and/or PPAR-γ. For example, in one embodiment the invention provides methods of treating or preventing Alzheimer's disease and diabetes.

In another aspect, the invention provides a method of treating or preventing a disease or disorder associated with PPAR-β/δ and/or PPAR-γ in a subject in need thereof. As used herein, the term "disease or disorder associated with PPAR-β/δ and/or PPAR-γ" refers to any disease, disorder, or condition which is caused or characterized by the activity of PPAR-β/δ and/or PPAR-γ. Exemplary diseases or disorders associated with PPAR-β/δ and/or PPAR-γ include, but are not limited to Alzheimer's disease, diabetes, and reduced cognitive function.

In another aspect, the invention provides a method of treating or preventing Alzheimer's disease or diabetes in a subject in need thereof. In one embodiment, the method comprises administering to the subject an effective amount of a composition comprising a compound of the invention. In one embodiment, diabetes includes, but is not limited to, pre-diabetes mellitus, diabetes mellitus, diabetes mellitus type 1 (T1DM), diabetes mellitus type 2 (T2DM), pre-diabetes (insulin resistance) and gestational diabetes.

In another aspect, the invention provides a method of improving cognition in a subject in need thereof. In one embodiment, the method comprises administering to the subject an effective amount of a composition comprising a compound of the invention.

The method of the invention may be used to activate or increase the activity or levels of PPAR-β/δ and/or PPAR-γ or treat or prevent a disease or disorder associated with PPAR-β/δ and/or PPAR-γ, such as Alzheimer's disease or diabetes in any subject in need thereof. In one embodiment, the subject is a mammal, including, but not limited to, a human, primate, cow, horse, sheep, goat, dog, cat, rodent, and the like.

In one embodiment, the method further comprises administering to the subject at least one additional therapeutic agent. In one embodiment, the therapeutic agent is selected from the group consisting of a diabetes therapeutic, Alzheimer's diease therapeutic, a therapeutic which improves cognition, and any combination thereof. For example, the composition of the invention may be administered with anti-diabetic agents. In one embodiment, the composition of the invention is administered in combination with insulin.

The composition of the invention may be administered to a patient or subject in need in a wide variety of ways. Modes of administration include intraoperatively intravenous, intravascular, intramuscular, subcutaneous, intracerebral, intraperitoneal, soft tissue injection, surgical placement, arthroscopic placement, and percutaneous insertion, e.g., direct injection, cannulation or catheterization. Any administration may be a single application of a composition of invention or multiple applications. Administrations may be to single site or to more than one site in the individual to be treated. Multiple administrations may occur essentially at the same time or separated in time.

In one embodiment, the invention includes a method comprising administering a combination of compounds and/or therapeutics described herein. In certain embodiments, the method has an additive effect, wherein the overall effect of administering the combination of compounds is approximately equal to the sum of the effects of administering each individual compound. In other embodiments, the method has a synergistic effect, wherein the overall effect of administering a combination of compounds is greater than the sum of the effects of administering each individual compound. A synergistic effect may be calculated, for example, using suitable methods such as, for example, the Sigmoid-Emax equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

The method comprises administering a combination of therapeutics in any suitable ratio. For example, in one embodiment, the method comprises administering three individual therapeutics at a 1:1:1 ratio. In one embodiment, the method comprises administering two individual therapeutics at a 1:1 ratio. However, the method is not limited to any particular ratio. Rather any ratio that is shown to be effective is encompassed.

Combination Therapies

The compounds of the present invention may be useful in combination with one or more additional compounds. In certain embodiments, these additional compounds may comprise compounds of the present invention or therapeutic agents which are known anti-diabetic agents. In certain embodiments, the anti-diabetes agent may comprise compounds useful for treating diabetes. Such compounds include, but are not limited to, compounds which are known to treat, prevent, or reduce the symptoms of diabetes.

In certain embodiments, these additional compounds may comprise compounds of the present invention or therapeutic agents which are known anti-diabetic agents. In certain embodiments, the anti-diabetes agent may comprise compounds useful for treating diabetes. Such compounds include, but are not limited to, compounds which are known to treat, prevent, or reduce the symptoms of diabetes.

In non-limiting examples, the compounds useful within the invention may be used in combination with one or more of the following diabetes drugs: insulin, GLP-1 agonists, dual GLP-1/glucagon agonists, GIP agonists, somatostatin sst3 antagonists, DGAT1 inhibitors, methfionine aminopeptidase 2 (MetAP2) inhibitors, GPR142 agonists, AMPK activators, GLP-1R positive allosteric modulators (PAMs), GPR119 agonists, CB1 receptor antibodies, peripherally-restricted small molecule CB1 antagonists, GRK2 inhibitors, GPR39 agonists, GPR40 agonists, GPR120 agonists, MC4R agonists, glucokinase activators, MCHR1 antagonists, OGT activators, glucagon receptor antagonists, fatty acid-binding protein aP2 antibodies, selective Kv1.3 channel blockers, asprosin, dextromethorphan, FGF1, celastrol, DPP4 inhibitors, SGLT-2 inhibitors, secretagogues such as sulfonylurea, tolbutamide, acetohexamide, tolazamide, chlorpropamide, glipizide, glyburide, glimepiride, glibenclamide, gliclazide, meglitinide such as nateglinide, senaglinide, repaglinide, insulin sensitizers such as biguanides, metformin, thiazolidinediones such as rosiglitazone, isaglitazone, darglitazone, englitazone, and pioglitazone.

In certain embodiments, these additional compounds may comprise compounds of the present invention or therapeutic agents which are known anti-Alzheimer's disease agents. In certain embodiments, the anti-Alzheimer's disease agent may comprise compounds useful for treating Alzheimer's disease. Such compounds include, but are not limited to, compounds which are known to treat, prevent, or reduce the symptoms of Alzheimer's disease.

In non-limiting examples, the compounds useful within the invention may be used in combination with one or more of the following Alzheimer's disease treatments: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; GABAA inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

In one embodiment, the invention includes a method comprising administering a combination of a compound of the invention as described elsewhere herein and an additional therapeutic agent. In certain embodiments, the method has an additive effect, wherein the overall effect of the administering the combination of a compound of the invention and an additional therapeutic agent is approximately equal to the sum of the effects of administering each individually. In other embodiments, the method has a synergistic effect, wherein the overall effect of administering a combination of compound of the invention and an additional therapeutic agent is greater than the sum of the effects of administering each individualy. A synergistic effect may be calculated, for example, using suitable methods such as, for example, the Sigmoid-Eurax equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Pharmaceutical Compositions, Administration, Dosage & Formulations

The invention also encompasses the use of pharmaceutical compositions of the invention or salts thereof to practice the methods of the invention. Such a pharmaceutical composition may consist of at least one compound of the invention or a salt thereof in a form suitable for administration to a subject, or the pharmaceutical composition may comprise at least one compound of the invention or a salt thereof, and one or more pharmaceutically acceptable carriers, one or more additional ingredients, or some combination of these. The compound of the invention may be present in the pharmaceutical composition in the form of a physiologically acceptable salt, such as in combination with a physiologically acceptable cation or anion, as is well known in the art.

In an embodiment, the pharmaceutical compositions useful for practicing the methods of the invention may be administered to deliver a dose of between 1 ng/kg/day and 100 mg/kg/day. In another embodiment, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for oral, rectal, vaginal, parenteral, topical, pulmonary, intranasal, buccal, ophthalmic, or another route of administration. A composition useful within the methods of the invention may be directly administered to the skin, or any other tissue of a mammal. Other contemplated formulations include liposomal preparations, resealed erythrocytes containing the active ingredient, and immunologically-based formulations. The route(s) of administration will be readily apparent to the skilled artisan and will depend upon any number of factors including the type and severity of the disease being treated, the type and age of the veterinary or human subject being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are formulated using one or more pharmaceutically acceptable excipients or carriers. In one embodiment, the pharmaceutical compositions of the invention comprise a therapeutically effective amount of a compound or conjugate of the invention and a pharmaceutically acceptable carrier. Pharmaceutically acceptable carriers that are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The regimen of administration may affect what constitutes an effective amount. The therapeutic formulations may be administered to the subject either before or after the onset of a disease or infection. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat the disease or infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or infection in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of a disease or infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the disease or infection in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the compound of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. In some aspects, the dosage of such compounds lies within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent a disease or infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for parenteral administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out certain embodiments of the present invention, and are not to be construed as limiting in any way the remainder of the disclosure.

Example 1

The data presented herein demonstrates that the inventive compounds, compound AU9-1 through compound AU9-8 (Table 1), have superior binding, and efficacy and lower toxicity compared to the comparative compound, compound 9. Compound masses and molecular formulae were confirmed by mass spectrometry (MS) experiments.

TABLE 1

Inventive compounds, molecular weights, and chemical structures.

| Compound | Monoisotopic Mass | Mol. Weight | Structure |
|---|---|---|---|
| 9 (Comparative) | 538.21 | 538.53 | 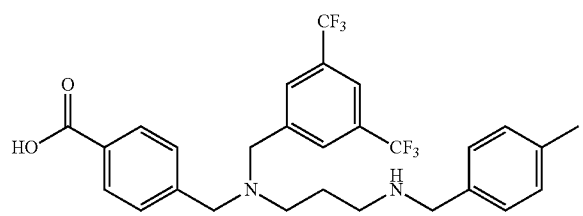 [SMILES: Cc1ccc(CNCCCN(Cc2ccc(C(=O)O)cc2)Cc2cc(C(F)(F)F)cc(C(F)(F)F)c2)cc1] |
| AU9-1 | 566.24 | 566.59 | 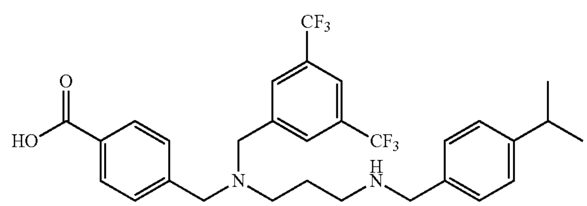 [SMILES: CC(C)c1ccc(CNCCCN(Cc2ccc(C(=O)O)cc2)Cc2cc(C(F)(F)F)cc(C(F)(F)F)c2)cc1] |
| AU9-2 | 552.22 | 552.56 | 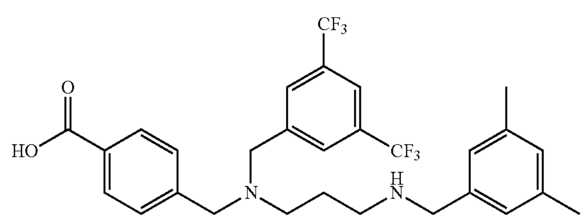 [SMILES: Cc1cc(C)cc(CNCCCN(Cc2ccc(C(=O)O)cc2)Cc2cc(C(F)(F)F)cc(C(F)(F)F)c2)c1] |
| AU9-3 | 580.25 | 580.62 | 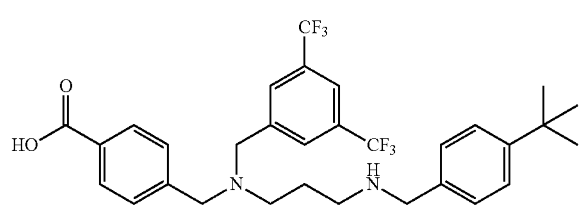 [SMILES: CC(C)(C)c1ccc(CNCCCN(Cc2ccc(C(=O)O)cc2)Cc2cc(C(F)(F)F)cc(C(F)(F)F)c2)cc1] |

TABLE 1-continued

Inventive compounds, molecular weights, and chemical structures.

| Compound | Monoisotopic Mass | Mol. Weight | Structure |
|---|---|---|---|
| AU9-4 | 538.21 | 538.53 | 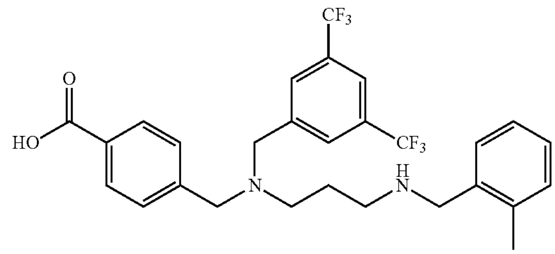 [SMILES: Cc1ccccc1CNCCCN(Cc1ccc(C(=O)O)cc1)Cc1cc(C(F)(F)F)cc(C(F)(F)F)c1] |
| AU9-5 | 552.22 | 552.56 | 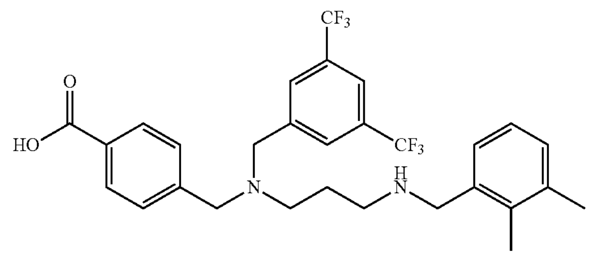 [SMILES: Cc1cccc(CNCCCN(Cc2ccc(C(=O)O)cc2)Cc2cc(C(F)(F)F)cc(C(F)(F)F)c2)c1C] |
| AU9-6 | 600.22 | 600.61 | 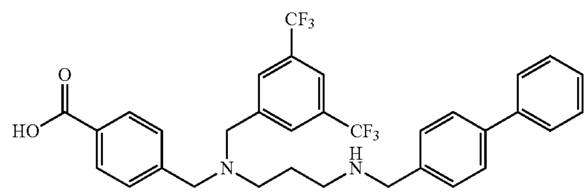 [SMILES: O=C(O)c1ccc(CN(CCCNCc2ccc(-c3ccccc3)cc2)Cc2cc(C(F)(F)F)cc(C(F)(F)F)c2)cc1] |
| AU9-7 | 600.22 | 600.61 | 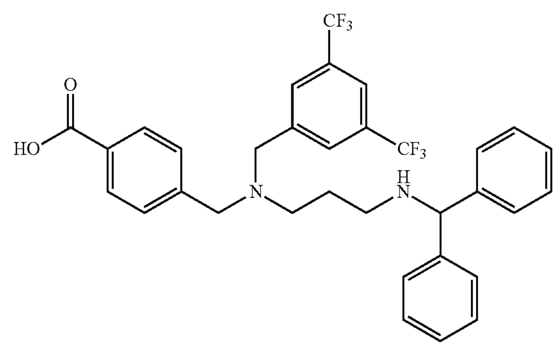 [SMILES: O=C(O)c1ccc(CN(CCCNC(c2ccccc2)c2ccccc2)Cc2cc(C(F)(F)F)cc(C(F)(F)F)c2)cc1] |
| AU9-8 | 524.19 | 524.51 | 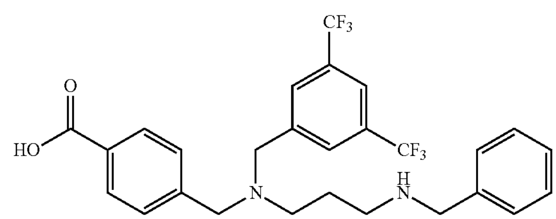 [SMILES: O=C(O)c1ccc(CN(CCCNCc2ccccc2)Cc2cc(C(F)(F)F)cc(C(F)(F)F)c2)cc1] |

Computational docking and molecular dynamics (MD) simulations were performed using the Schrödinger software package in order to assess and quantify the interactions between the inventive compounds and PPAR-γ. The results of the computational docking simulations are presented in Table 2. The results from the MD simulations, including ligand binding diagram, protein residue interactions, and protein/ligand root-mean-square deviation (RMSD), are presented in FIG. 1 through FIG. 15.

TABLE 2

Computational Docking scores of PPAR-ligands in the AF2 ligand binding of PPAR-γ.

| Compound | Docking score |
|---|---|
| AU9-1 | 9.88 |
| AU9-5 | 7.87 |
| AU9-2 | 6.85 |

TABLE 2-continued

Computational Docking scores of PPAR-
ligands in the AF2 ligand binding of PPAR-γ.

| Compound | Docking score |
|---|---|
| AU9-6 | 9.79 |
| AU9-3 | 7.4 |
| AU9-4 | 6.12 |
| AU9-8 | 6.32 |
| rosiglitazone | 4.332 |

Figure 16:
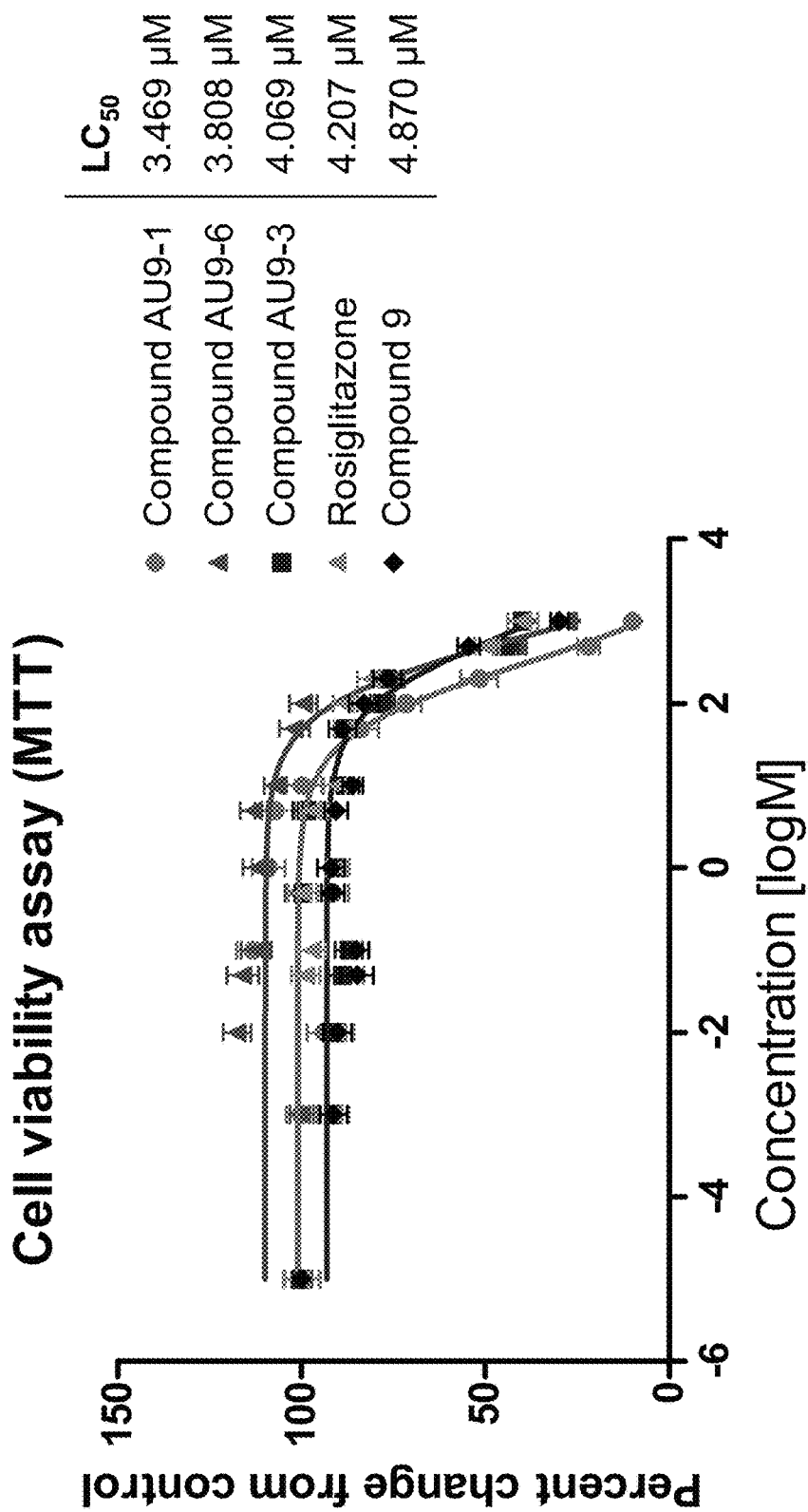
FIG. 16 depicts the results of a cell viability assay utilizing an MTT assay. LC$_{50}$ results for the inventive compounds and the comparative compounds rosiglitazone and compound 9 were calculated based on the plotted data.

A cell viability assay, performed via an MTT assay, tested for the concentration of drugs that lead to toxicity. The results of the MTT assay are presented in FIG. 16. The X-axis is concentration of drug on a log based scale. Concentrations from left to right were 1 nM, 10 nM, 100 nM, 500 nm, 1 μM, 5 μM, 10 μM, 50 μM, 100 μM, 200 μM, 500 μM and 1 mM. The lethal concentration at 50% ($LC_{50}$) is provided in the graph at μM concentrations.

Figure 17:
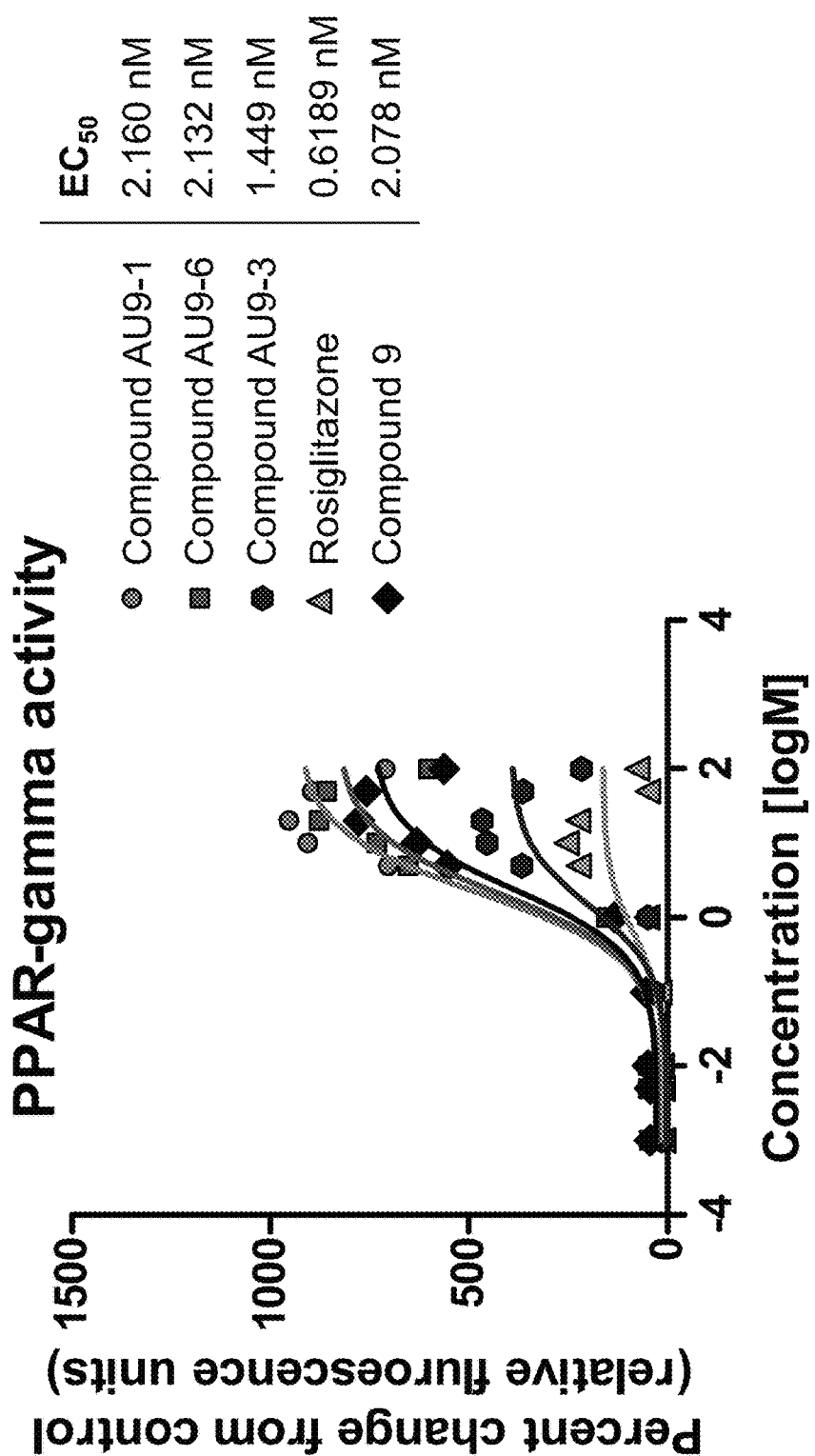
FIG. 17 depicts the results of a PPARγ activity assay. A Tyr473 to alanine mutation in human PPARγ was transfected into HEK293 cells+PPARγ (3XPPRE) vector with a luciferase tag for a promoter activity assay. PPARγ activity was then induced via treatment with the inventive compounds and the comparative compounds rosiglitazone and compound AU9. The resulting data were standardized to Beta-gal activity. The data represent a compilation of 4 independent assays.
Figure 18:
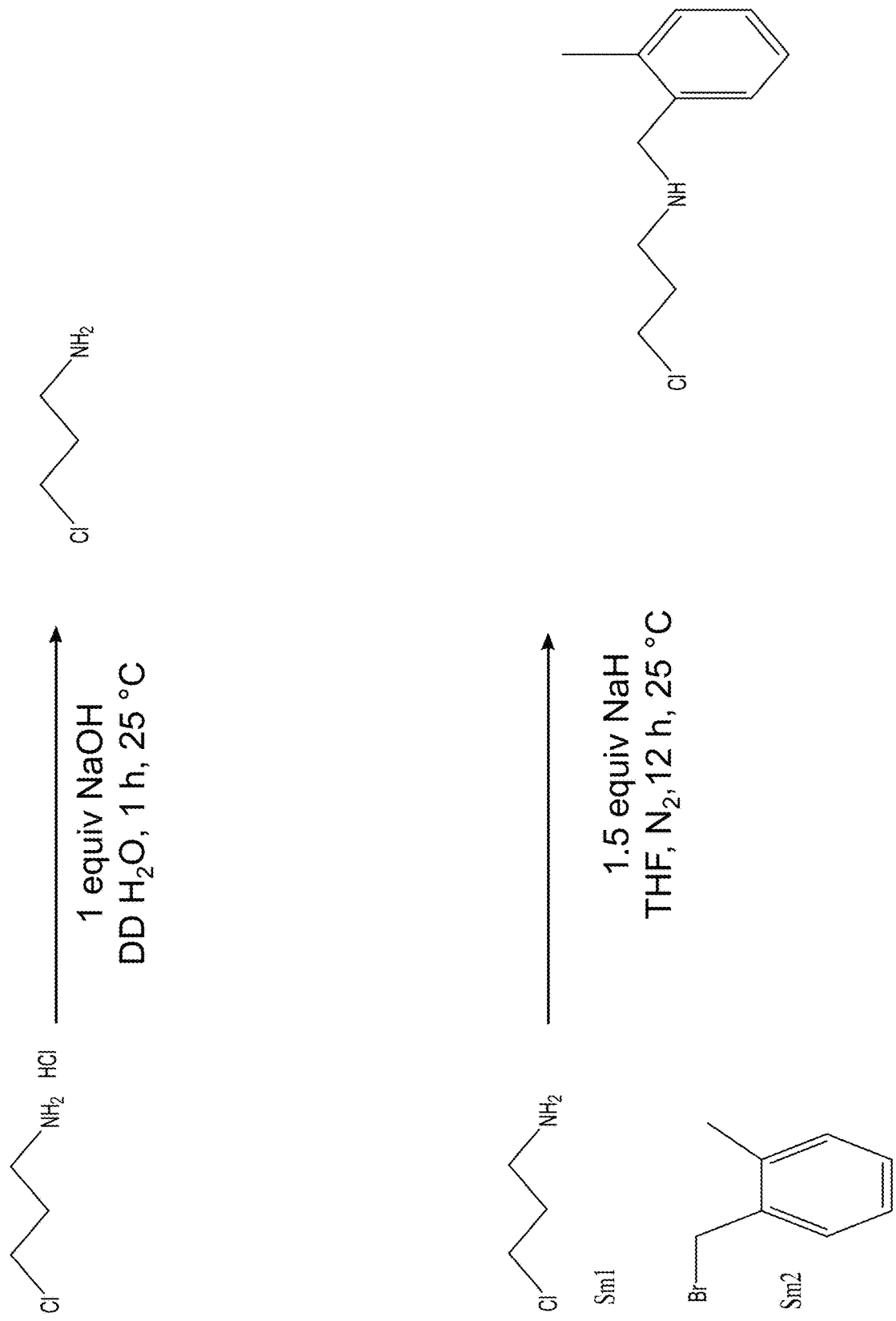
FIG. 18 is a scheme outlining the synthesis of compound AU9-4.
Figure 18:
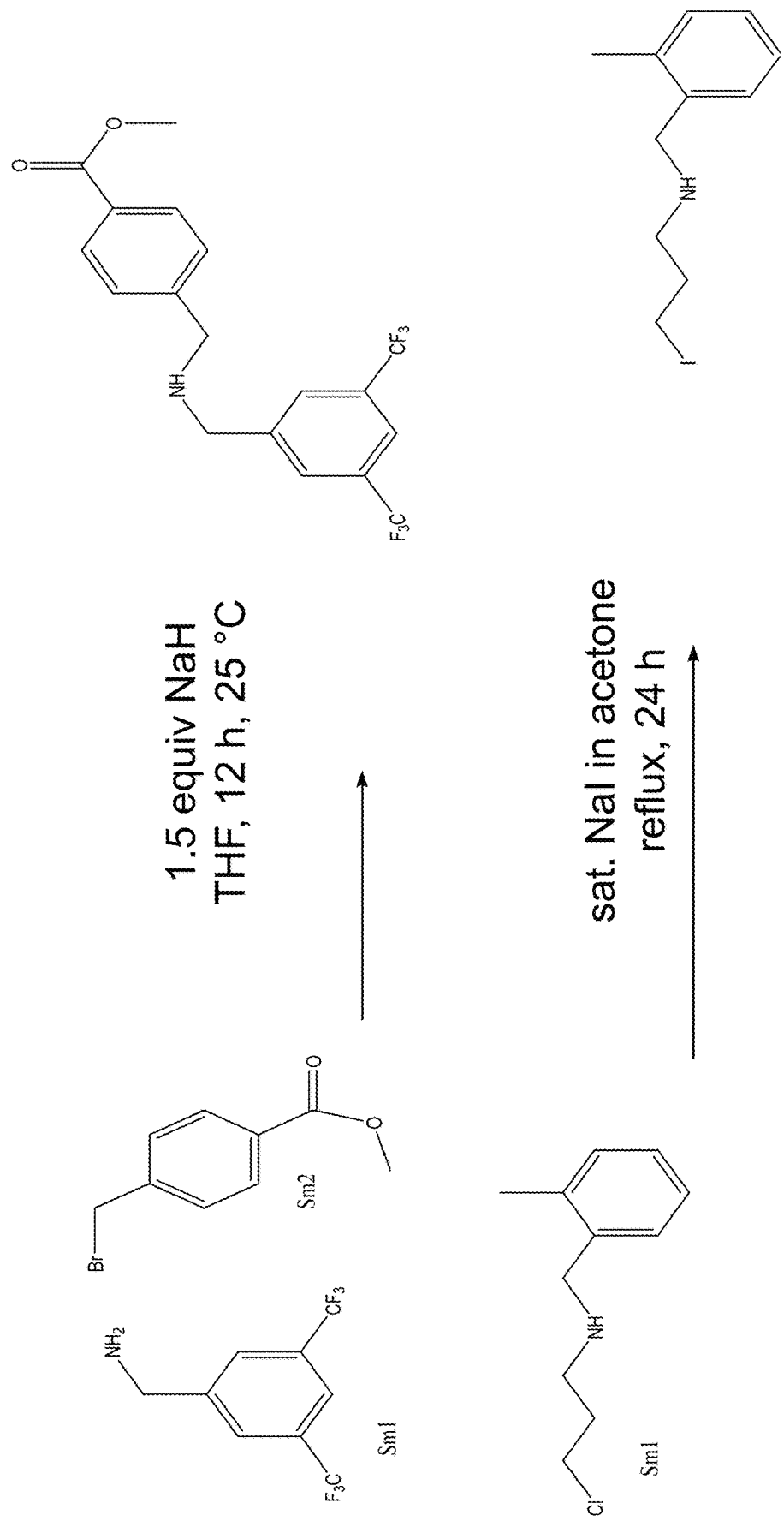
Figure 18:
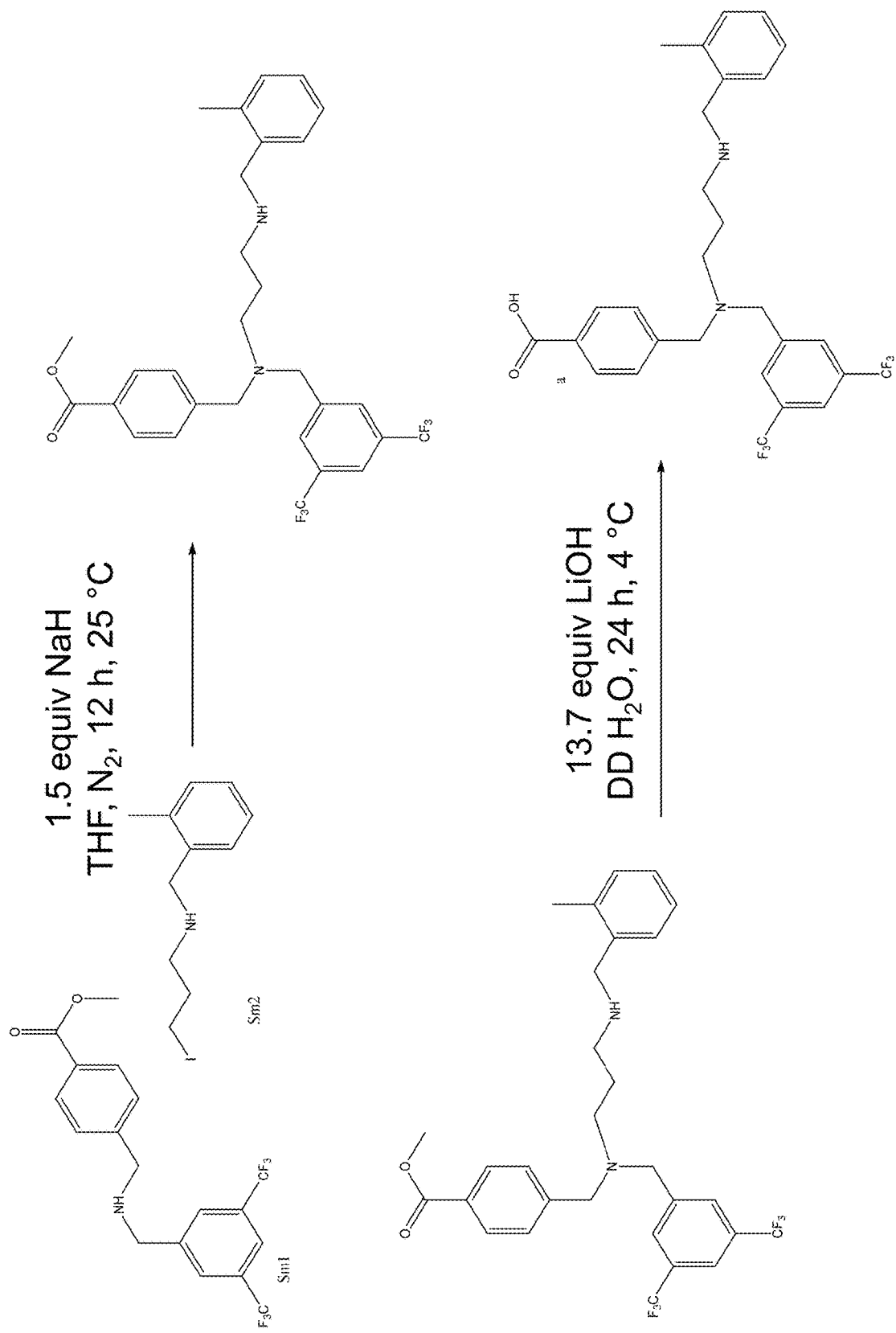
Figure 19:
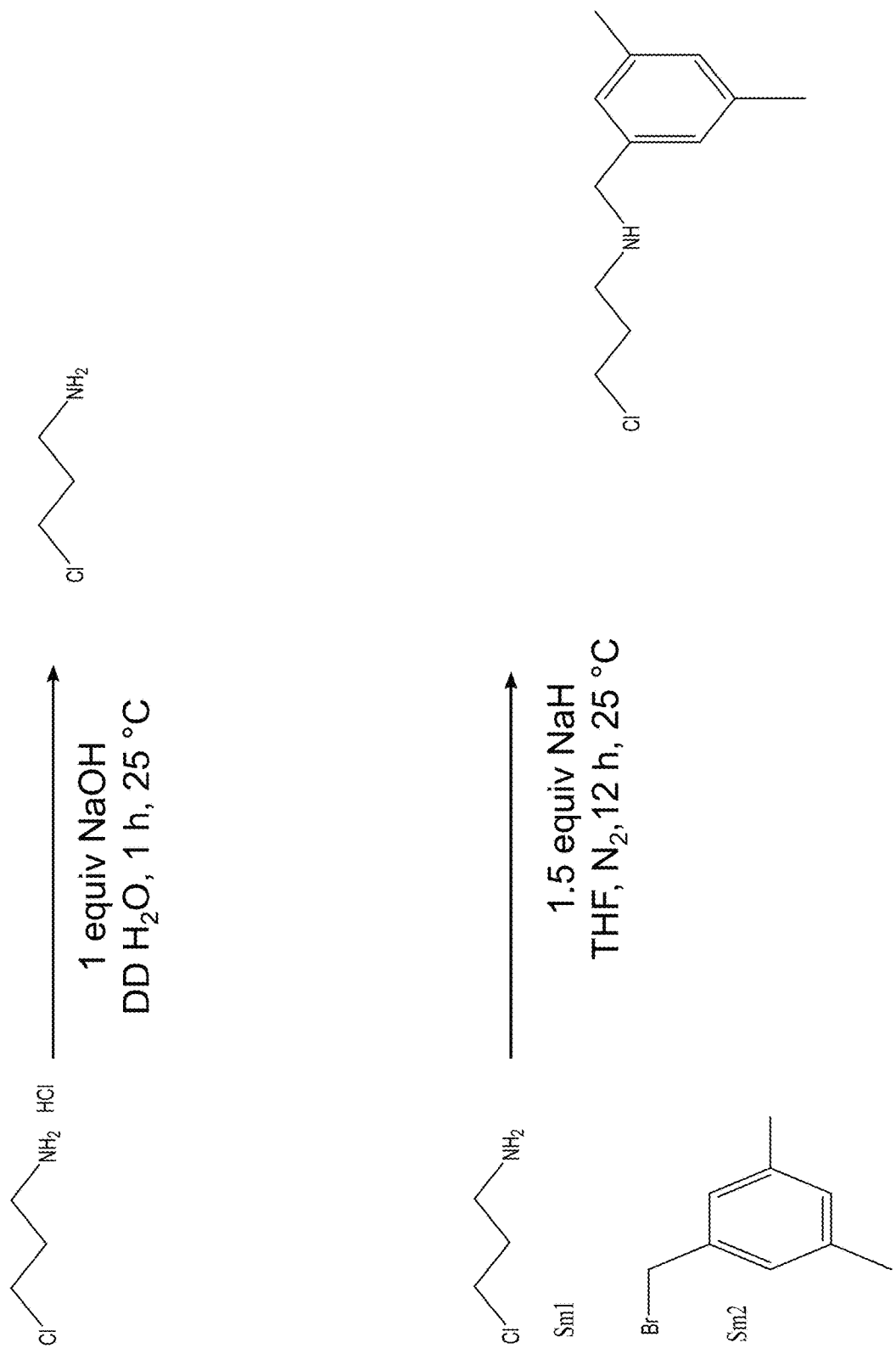
FIG. 19 is a scheme outlining the synthesis of compound AU9-2.
Figure 19:
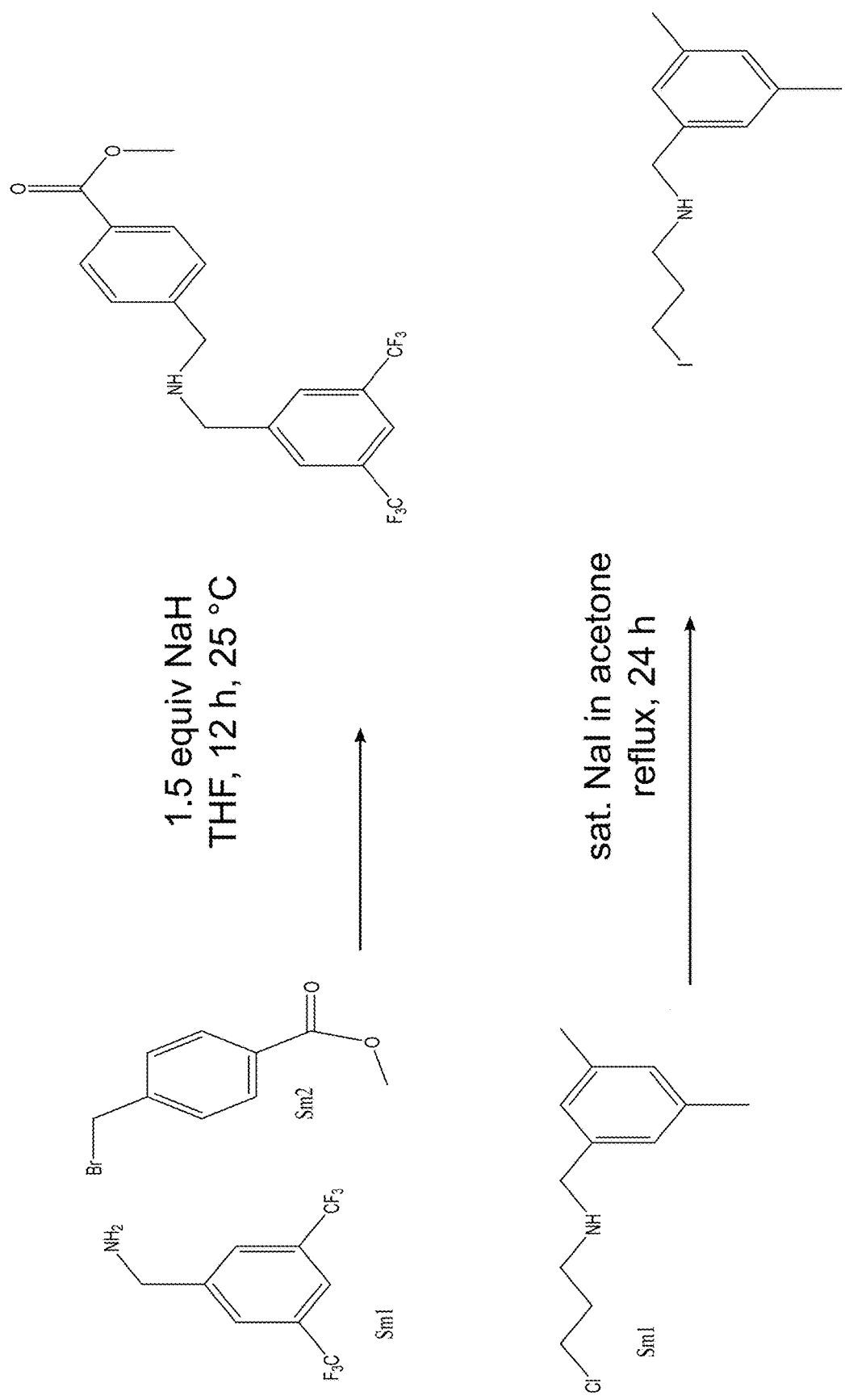
Figure 19:
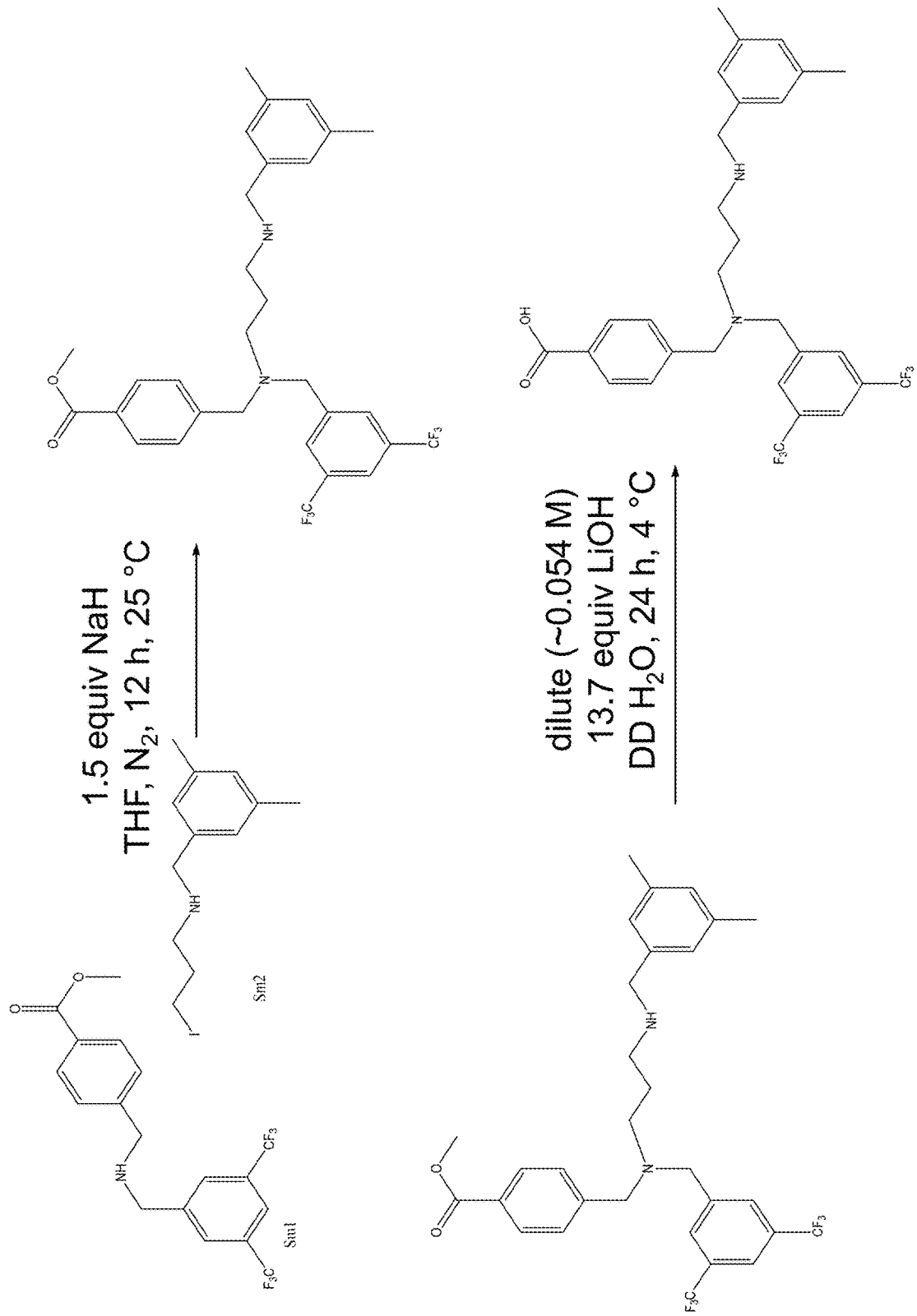
Figure 20:
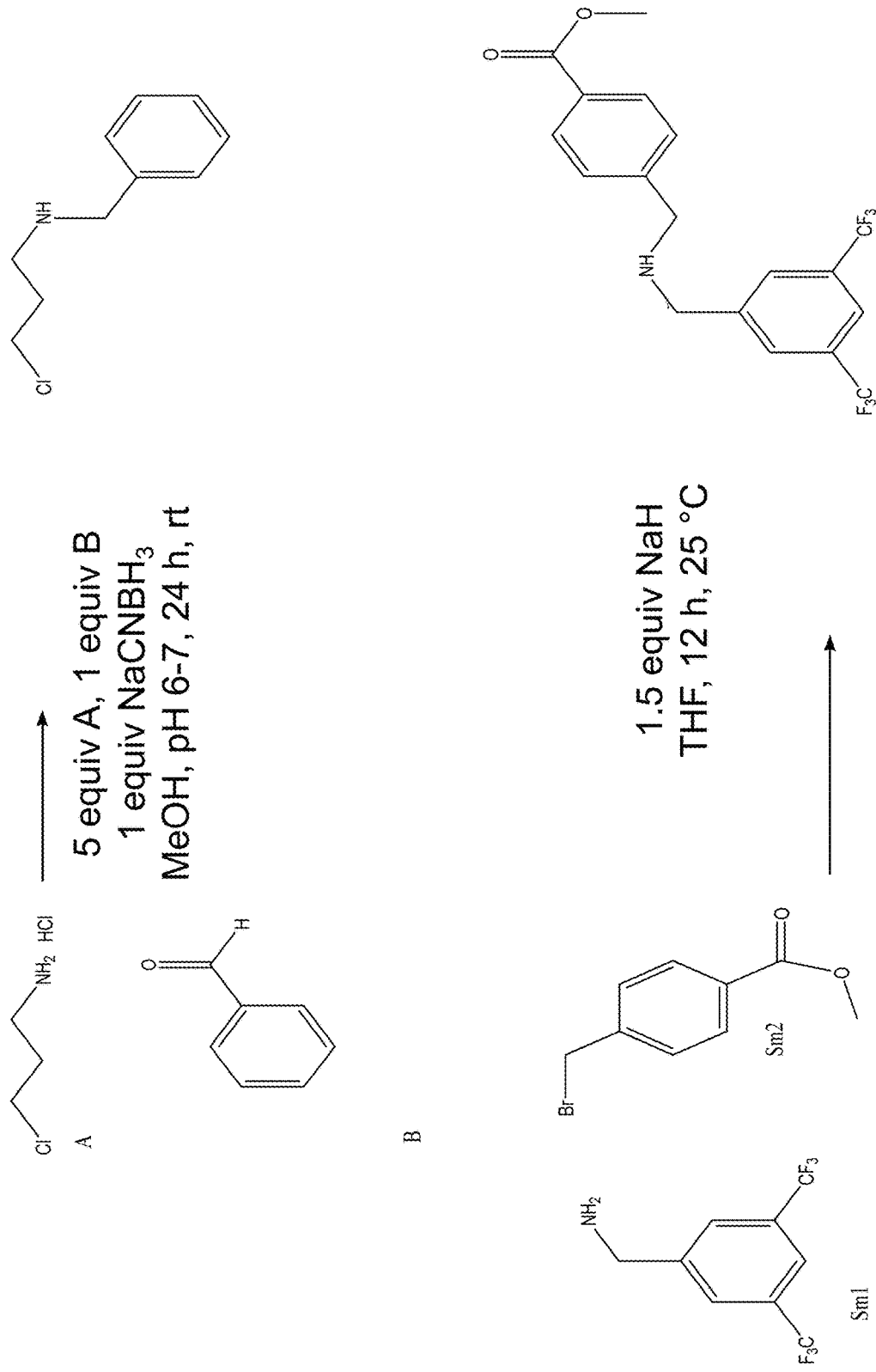
FIG. 20 is a scheme outlining the synthesis of compound AU9-8.
Figure 20:
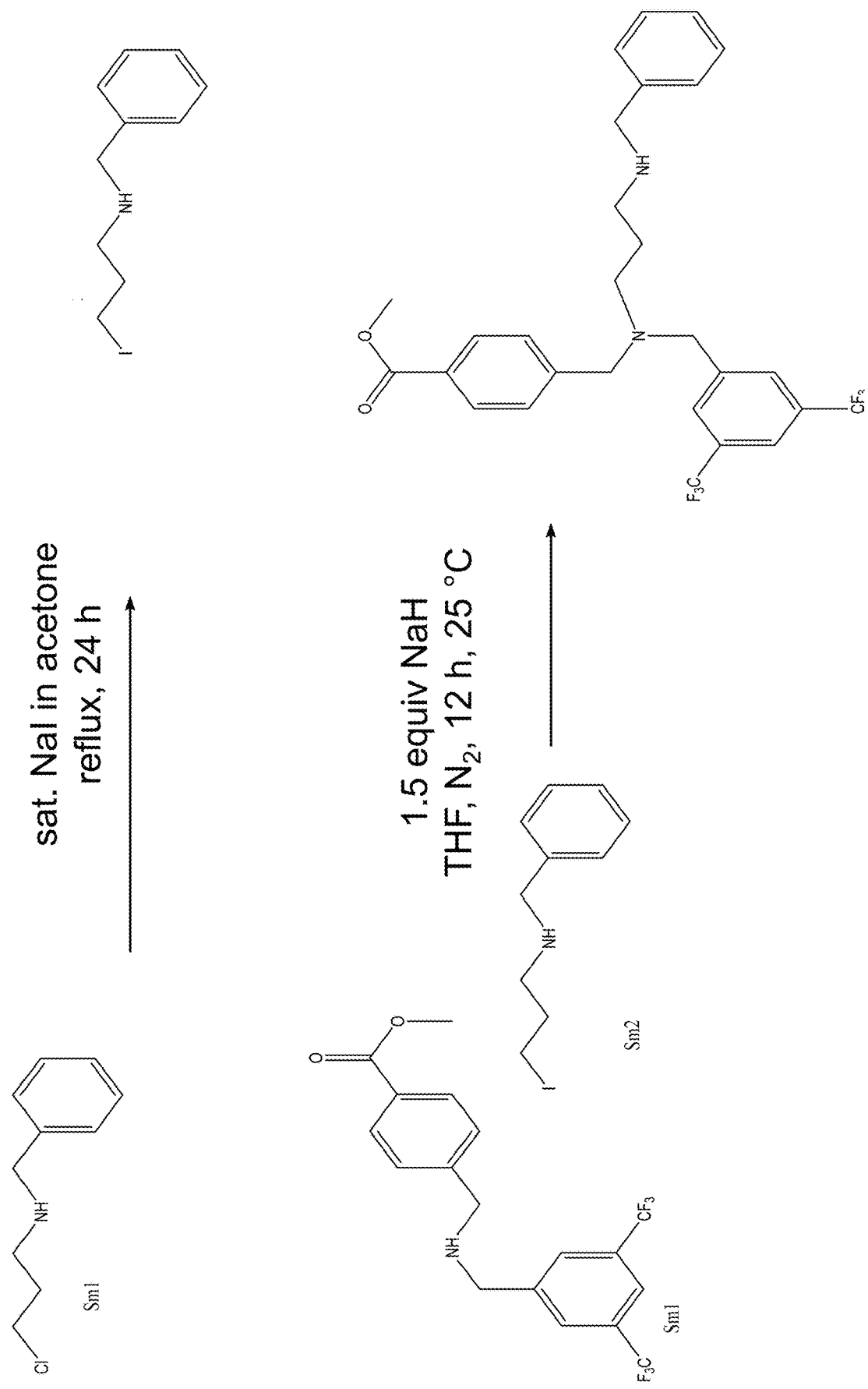
Figure 20:
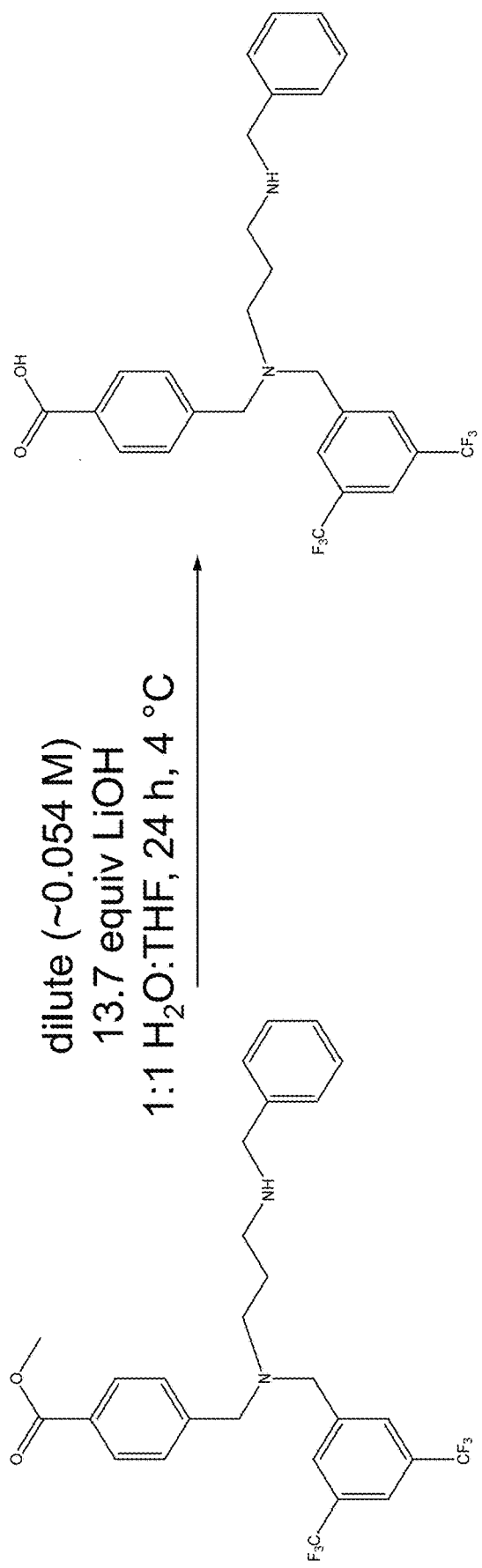
Figure 21:
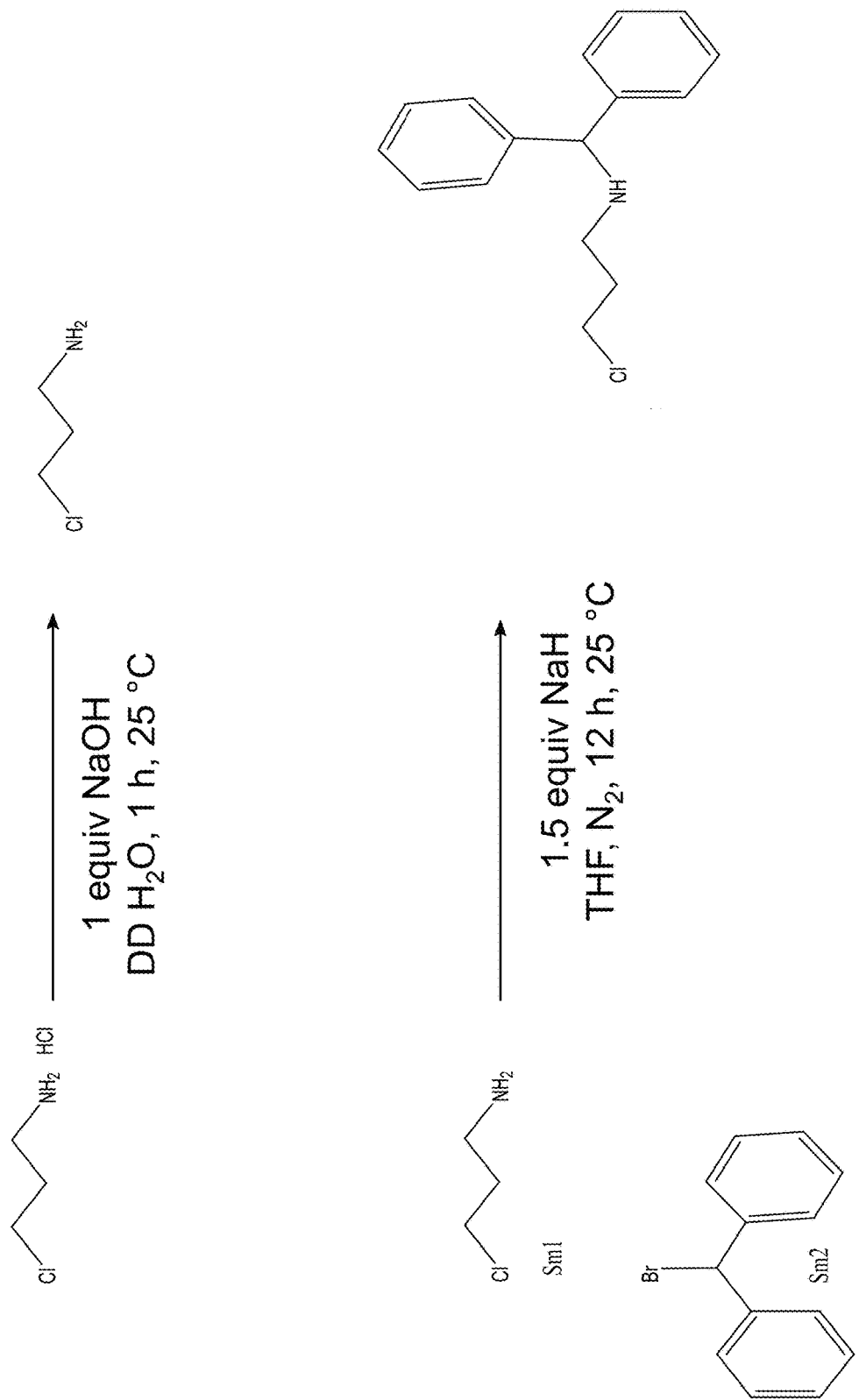
FIG. 21 is a scheme outlining the synthesis of compound AU9-7.
Figure 21:
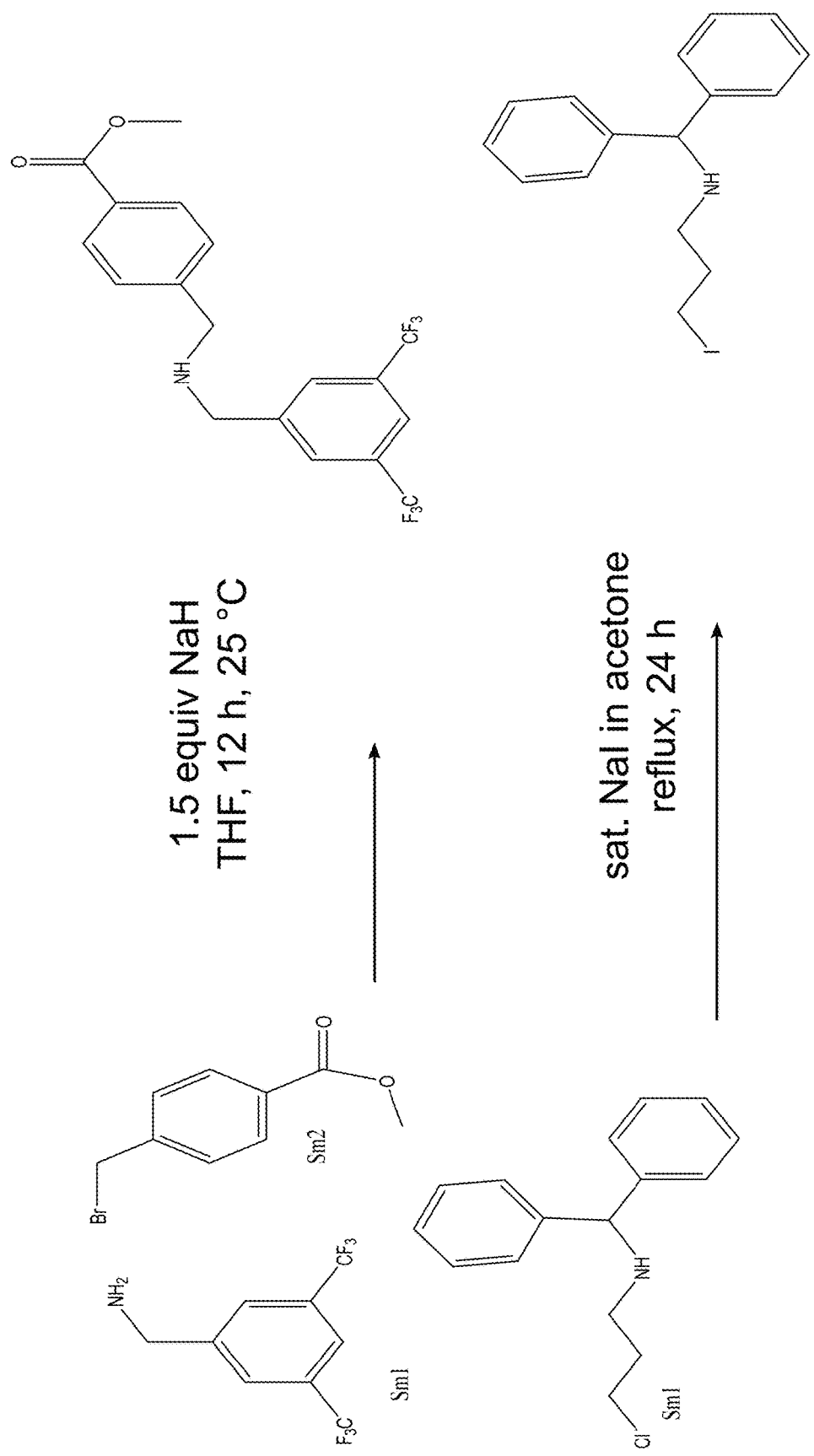
Figure 21:
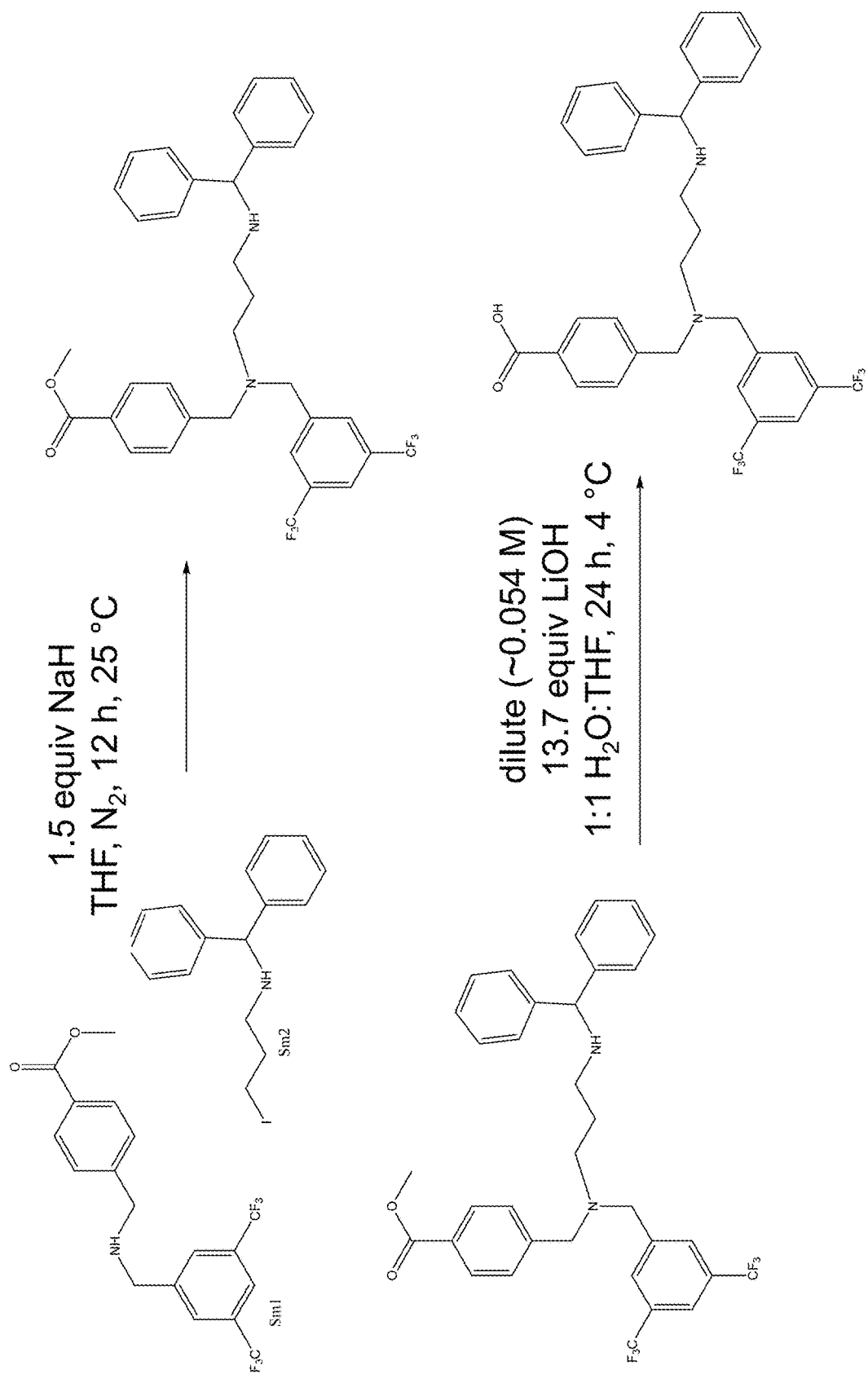
Figure 22:
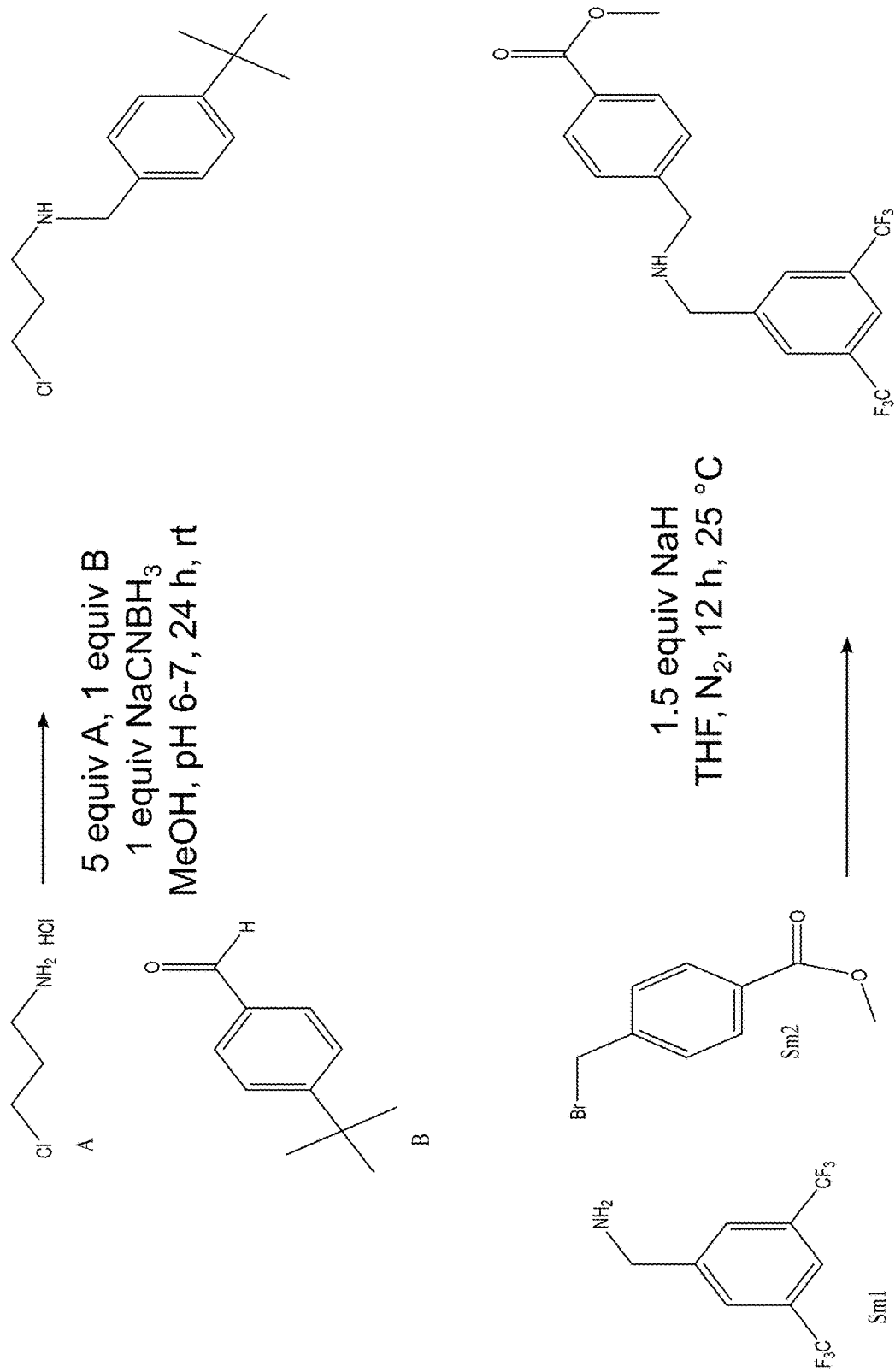
FIG. 22 is a scheme outlining the synthesis of compound AU9-3.
Figure 22:
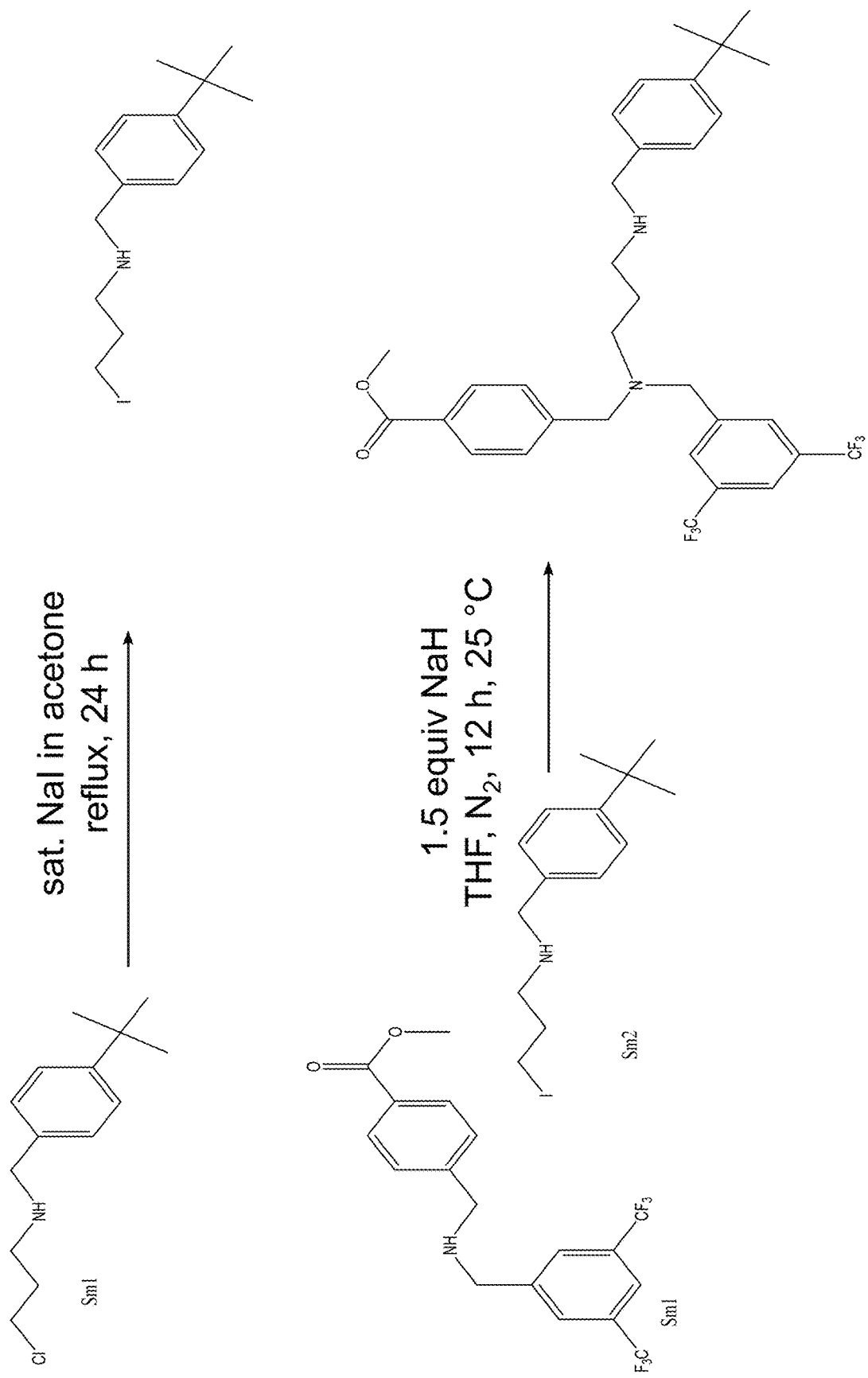
Figure 22:
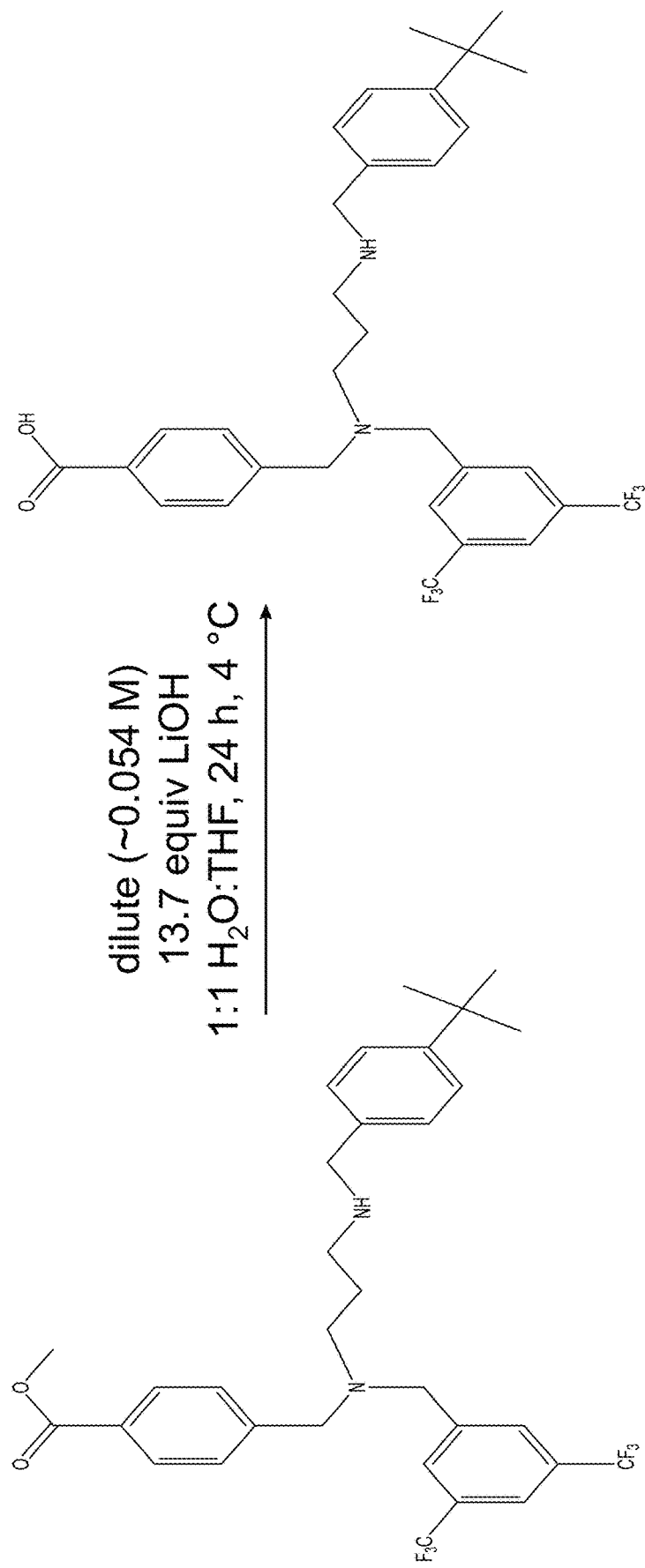
Figure 23:
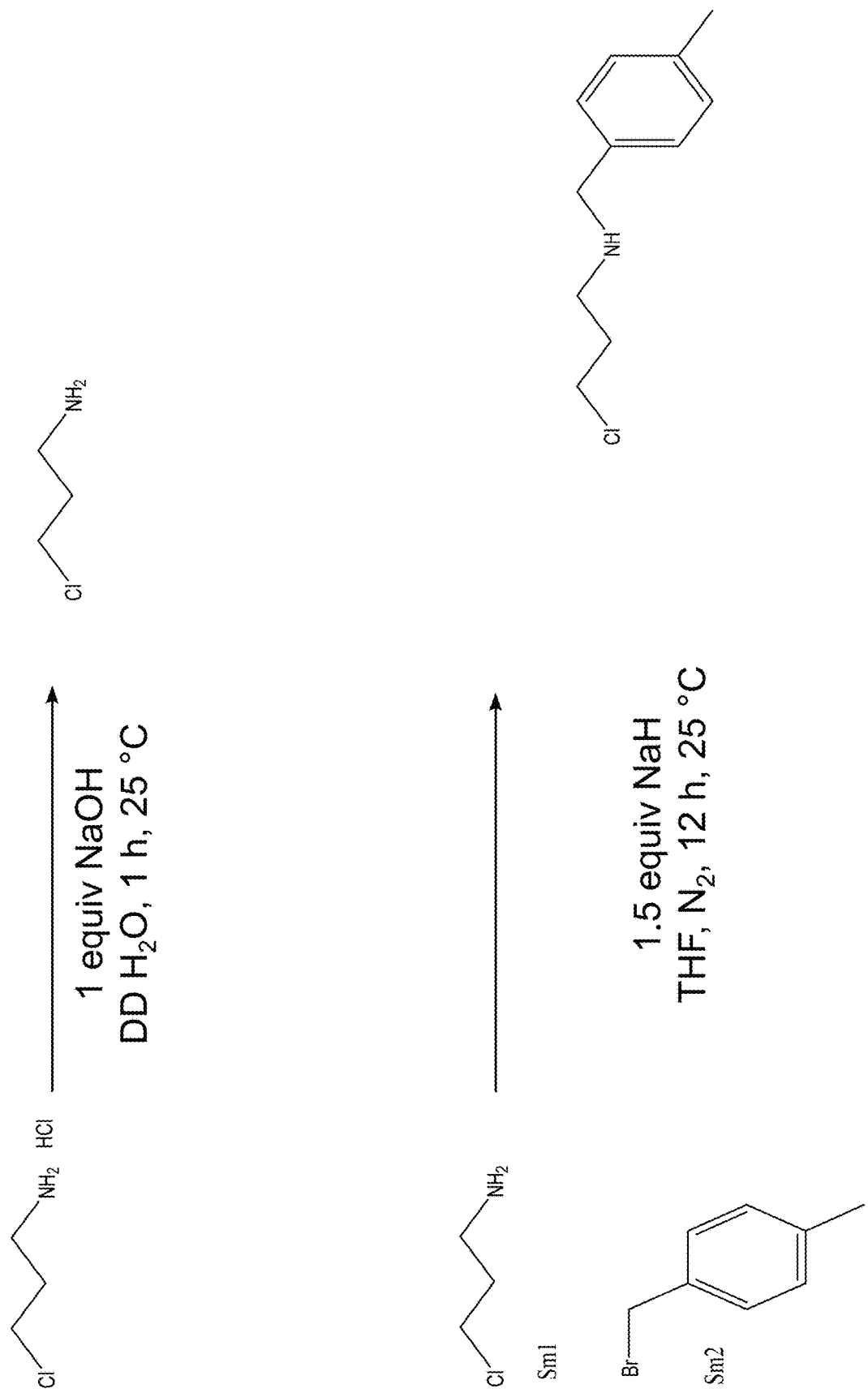
FIG. 23 is a scheme outlining the synthesis of comparative compound 9.
Figure 23:
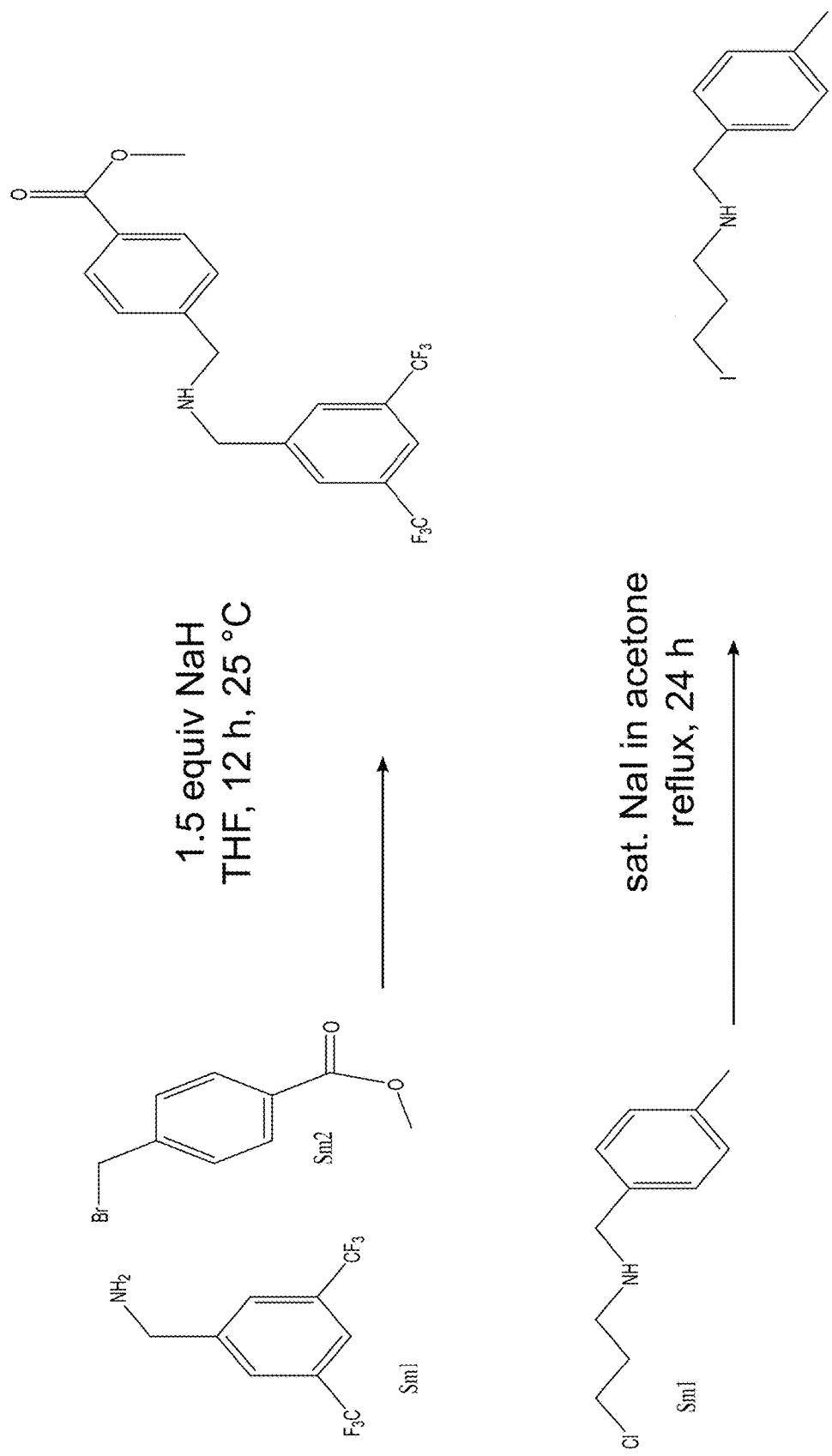
Figure 23:
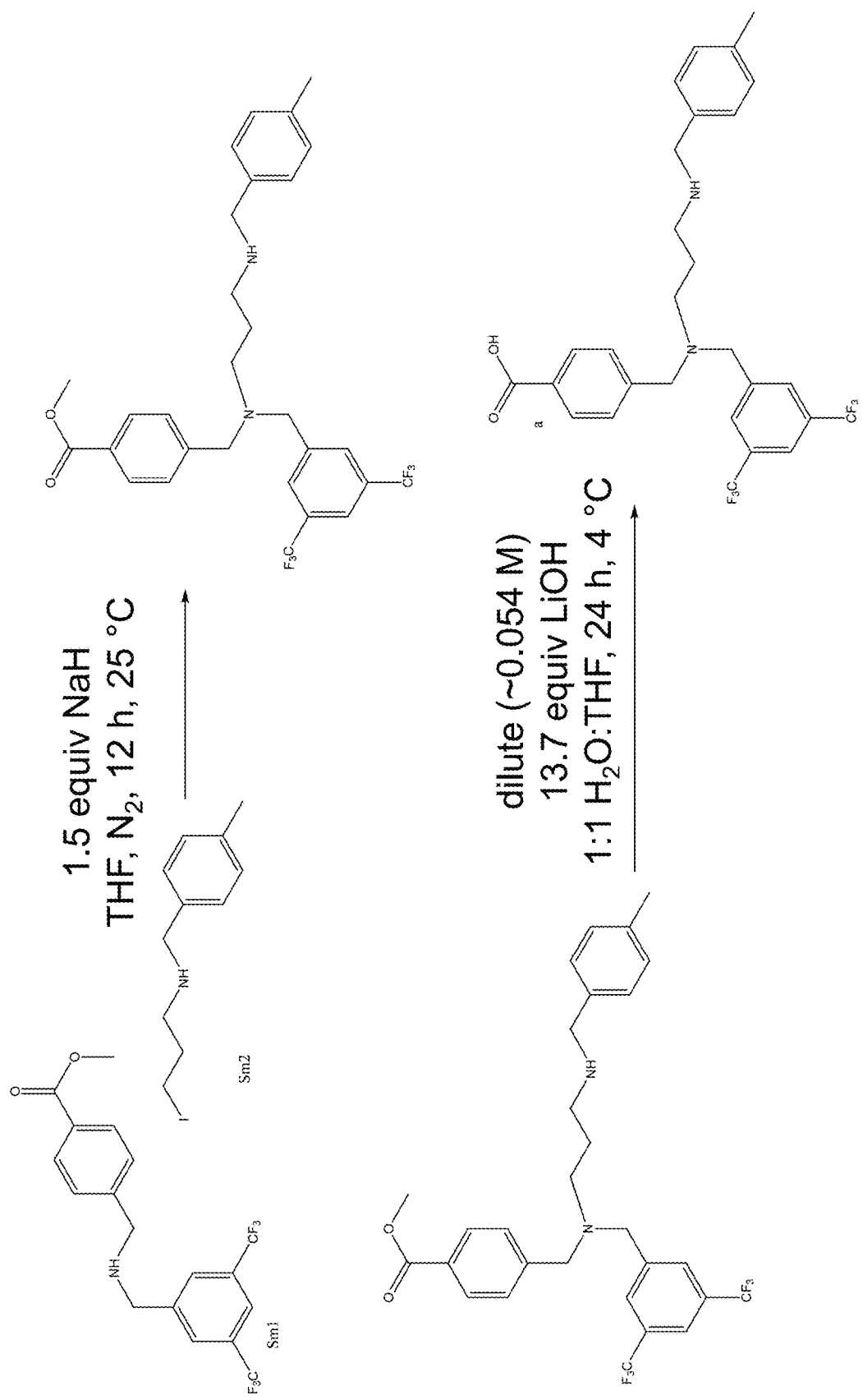
Figure 24:
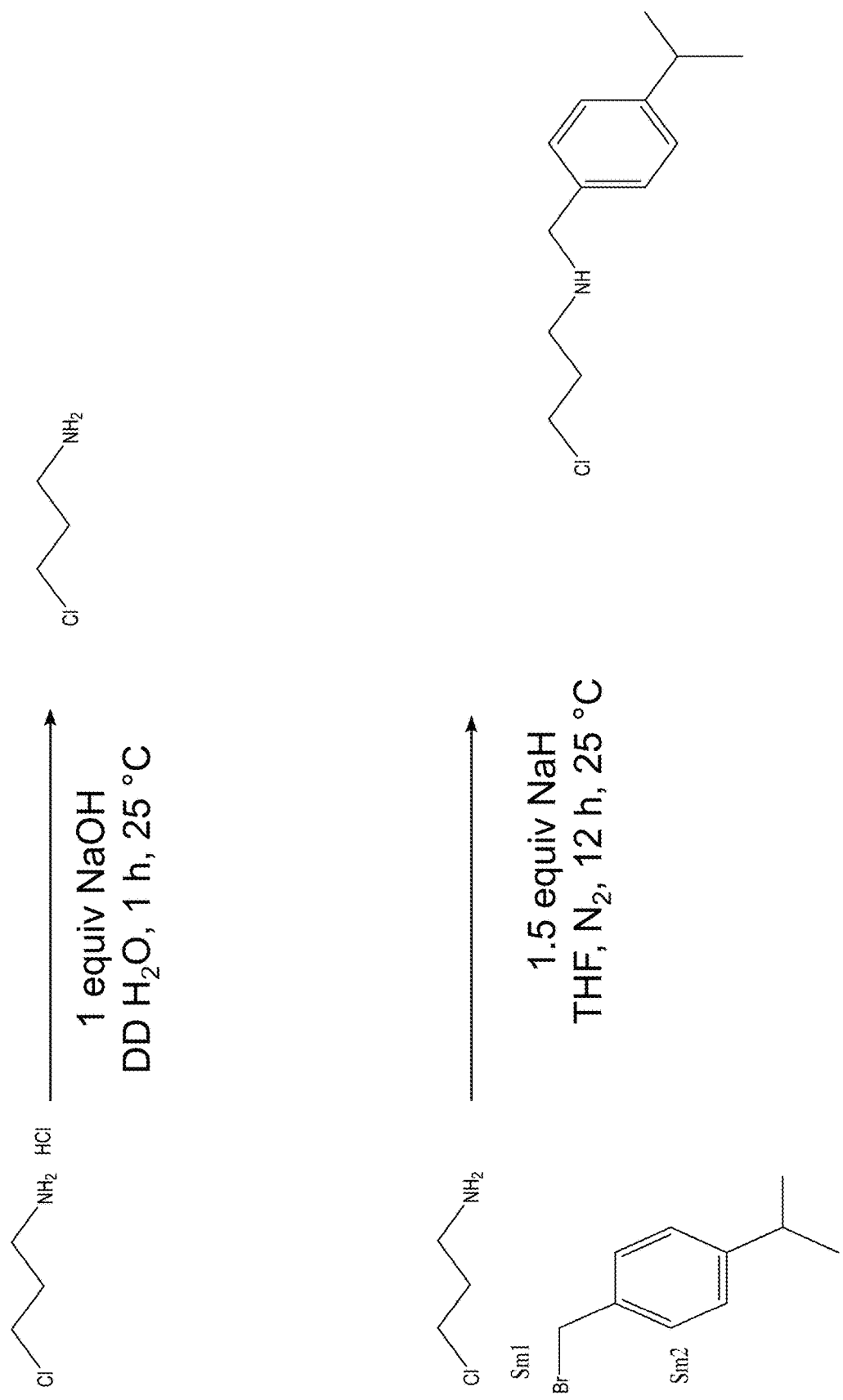
FIG. 24 is a scheme outlining the synthesis of compound AU9-1.
Figure 24:
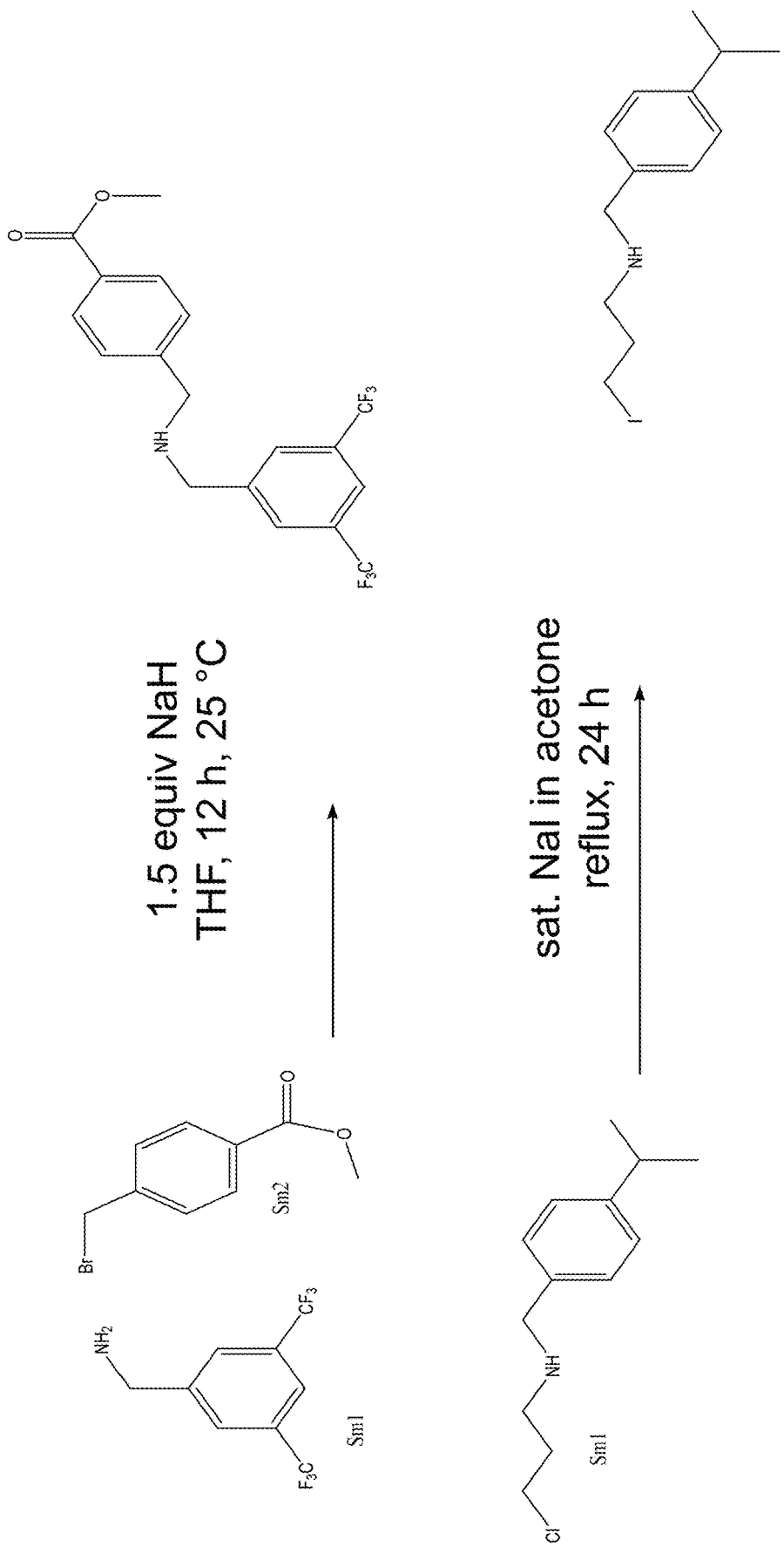
Figure 24:
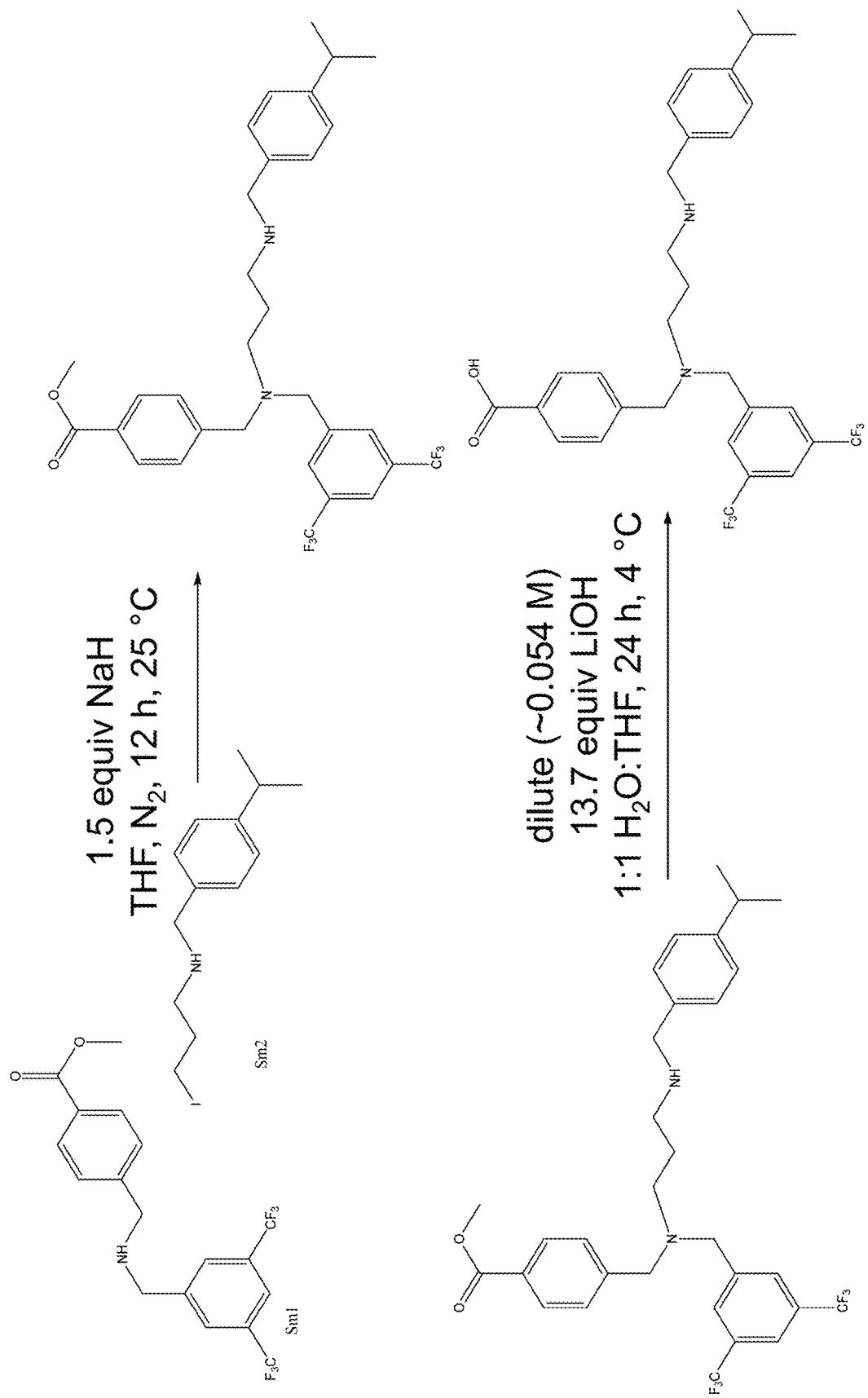

FIG. 17 depicts the results from a PPAR-γ activity assay. A Tyr473 to alanine mutation in human PPAR-γ was transfected into HEK293 cells+PPAR-γ (3XPPRE) vector with a luciferase tag for a promoter activity assay. PPAR-γ activity was then induced via treatment with the inventive compounds and the resulting data were standardized to Beta-gal activity. The data represent a compilation of 4 independent assays.

Synthetic procedures for compounds AU9-4, AU9-2, AU9-8, AU9-7, AU9-3, 9, and AU9-1 are provided in FIG. 18, FIG. 19, FIG. 20, FIG. 21, FIG. 22, FIG. 23, and FIG. 24, respectively.

The MD simulation of rosiglitazone (FIG. 10, FIG. 11, and FIG. 12) demonstrate that this TZD drug exhibits a significant binding interaction with the Tyrosine 473 residue of PPAR-γ, an interaction that has been shown to lead to deleterious effects such as increased incidences of cardiovascular effects. The PPAR-γ activity assay (FIG. 17) shows that mutation of Tyr473 to Ala abrogates binding between PPAR-γ and rosiglitazone.

Figure 2:
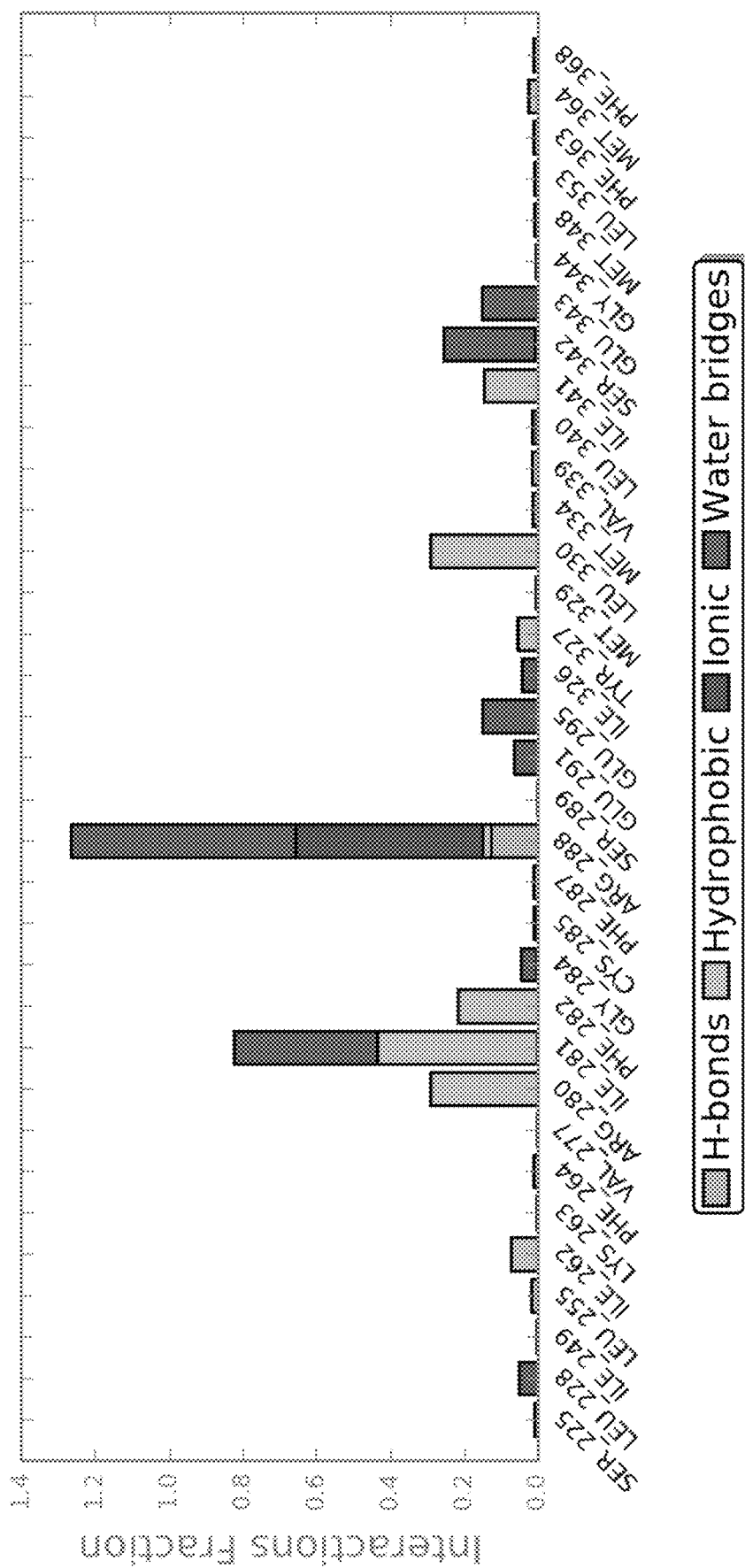
FIG. 2 is a plot of interactions between compound AU9-1 and protein PPARγ throughout an MD simulation. Protein-ligand interactions (or 'contacts') are categorized into four types: Hydrogen Bonds, Hydrophobic, Ionic and Water Bridges. The stacked bar charts are normalized over the course of the 100 ns MD trajectory.
Figure 3:
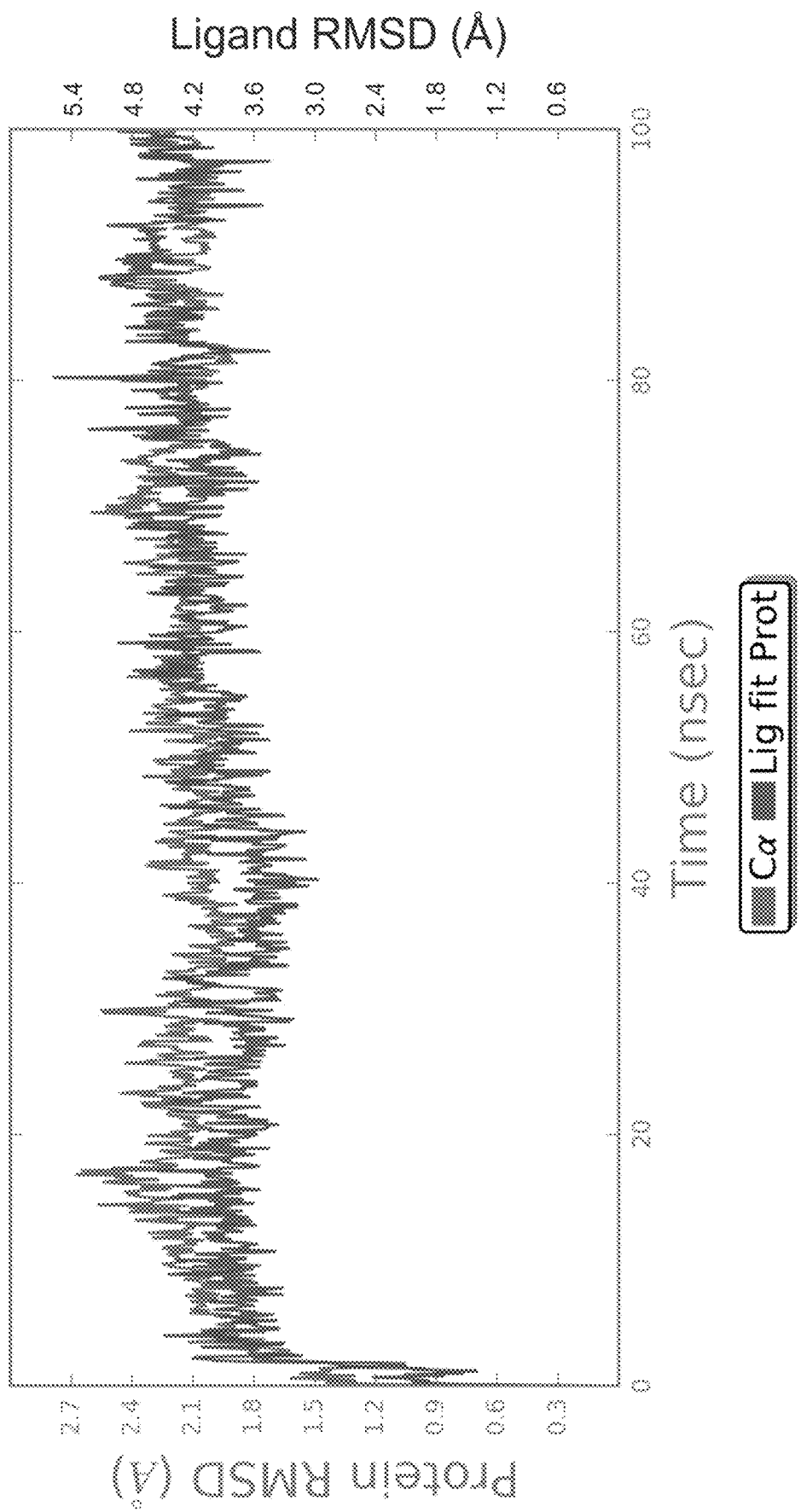
FIG. 3 is a plot of Protein-Ligand root-mean-square deviation (RMSD) for compound AU9-1 and PPARγ as a function of MD simulation time. All protein frames are first aligned on the reference frame backbone, and then the RMSD is calculated based on the atom selection (left y-axis). Ligand RMSD (right Y-axis) indicates how stable the ligand is with respect to the protein and its binding pocket.
Figure 4:
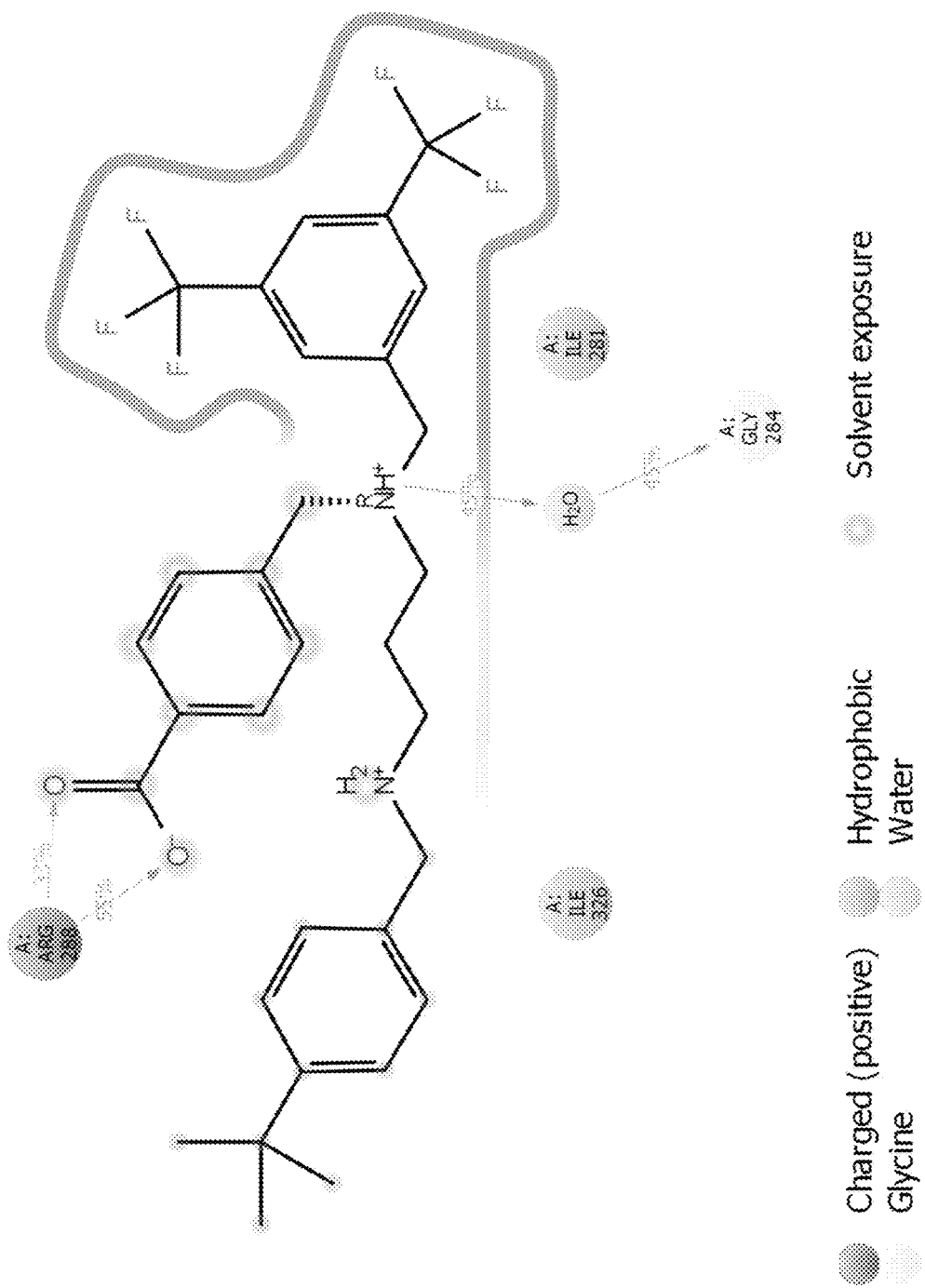
FIG. 4 is a schematic of detailed ligand atom interactions for compound AU9-3 with the PPARγ residues, derived from a 65 ns molecular dynamics (MD) simulation. Interactions that occur more than 30.0% of the simulation time in the selected trajectory (0.00 through 65.30 nsec), are shown.
Figure 5:
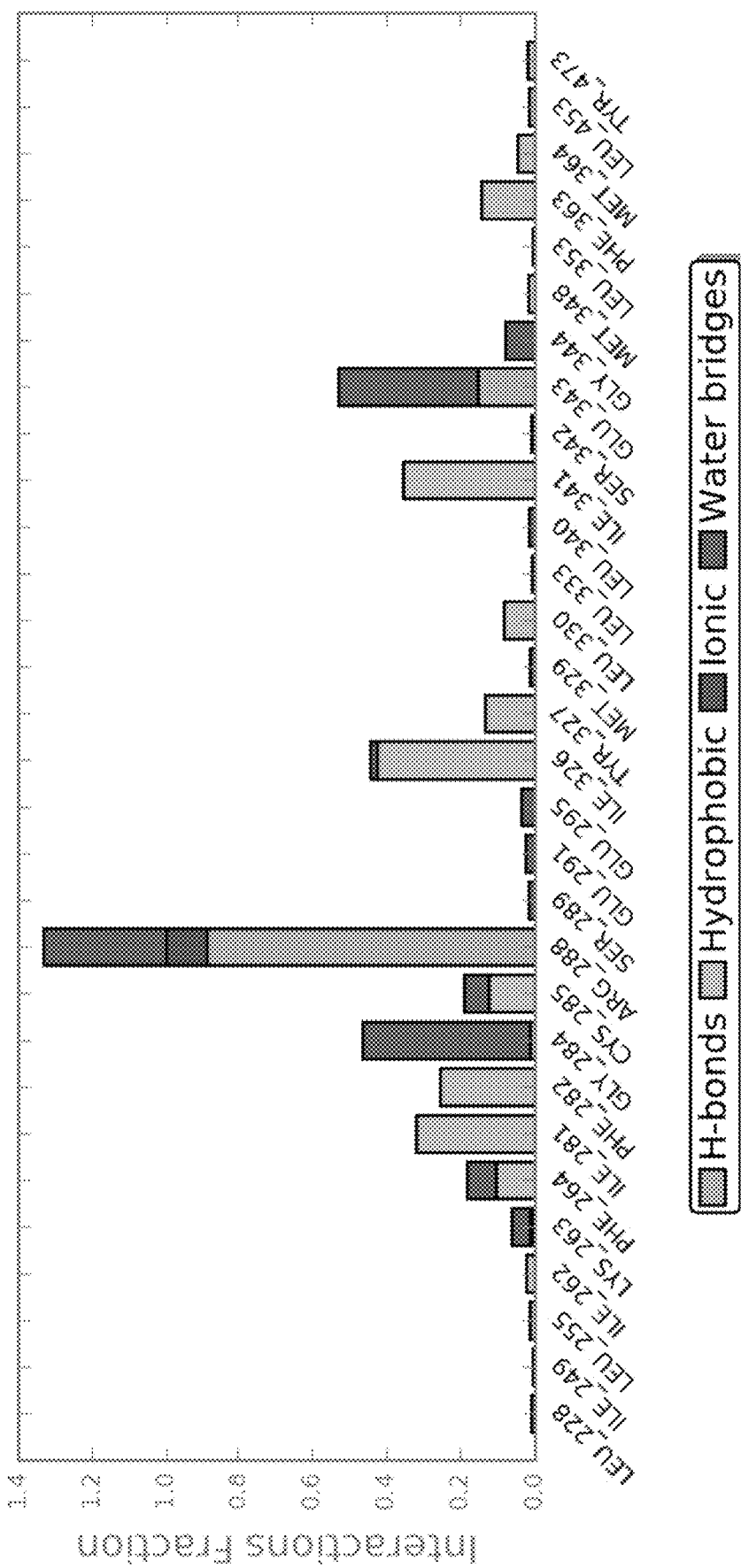
FIG. 5 is a plot of interactions between compound AU9-3 and protein PPARγ throughout an MD simulation. Protein-ligand interactions (or 'contacts') are categorized into four types: Hydrogen Bonds, Hydrophobic, Ionic and Water Bridges. The stacked bar charts are normalized over the course of the 65 ns MD trajectory.
Figure 6:
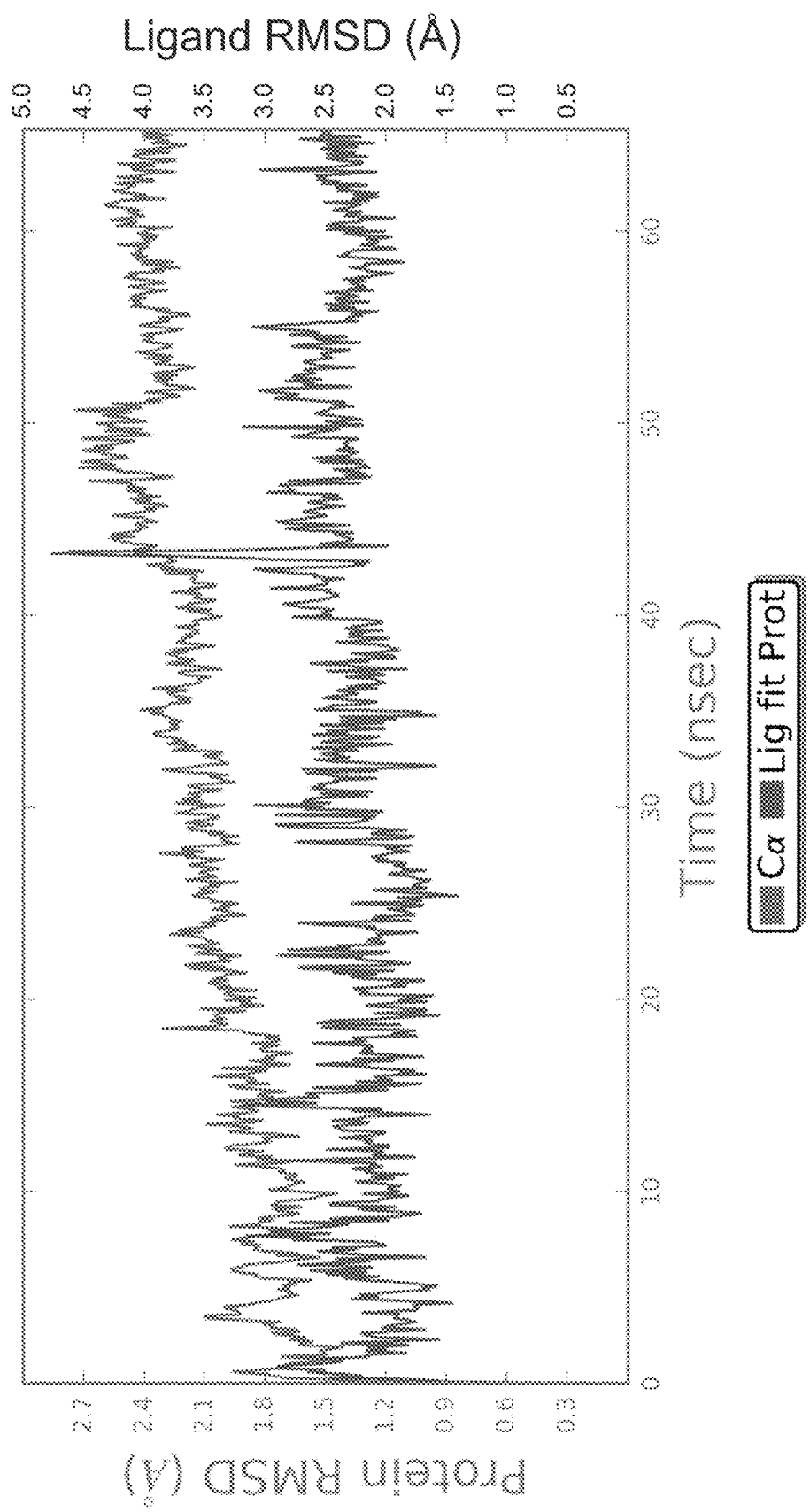
FIG. 6 is a plot of Protein-Ligand root-mean-square deviation (RMSD) for compound AU9-3 and PPARγ as a function of MD simulation time. All protein frames are first aligned on the reference frame backbone, and then the RMSD is calculated based on the atom selection (left y-axis). Ligand RMSD (right Y-axis) indicates how stable the ligand is with respect to the protein and its binding pocket.
Figure 7:
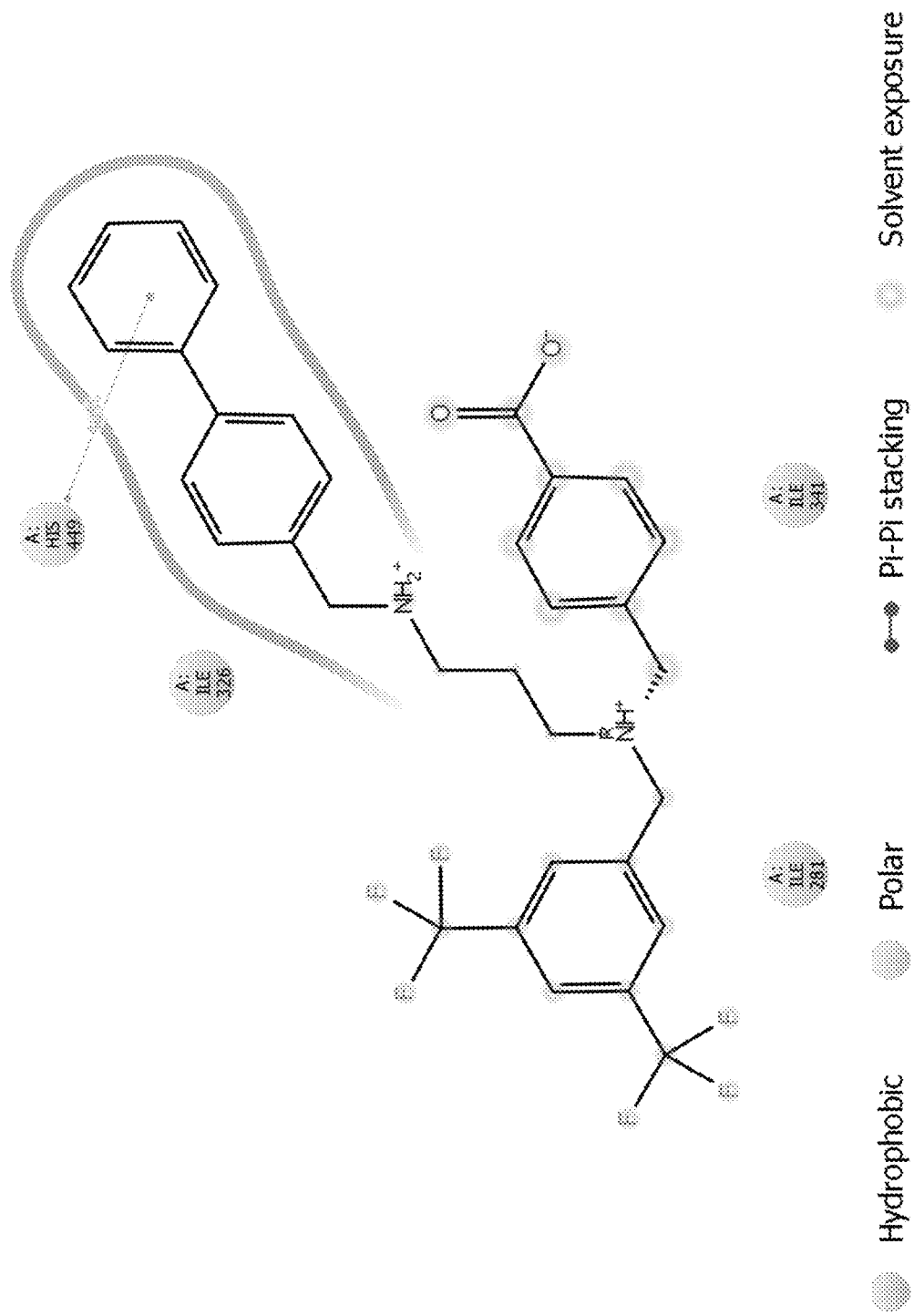
FIG. 7 is a schematic of detailed ligand atom interactions for compound AU9-6 with the PPARγ residues, derived from a 100 ns molecular dynamics (MD) simulation. Interactions that occur more than 30.0% of the simulation time in the selected trajectory (0.00 through 100.00 nsec), are shown.
Figure 8:
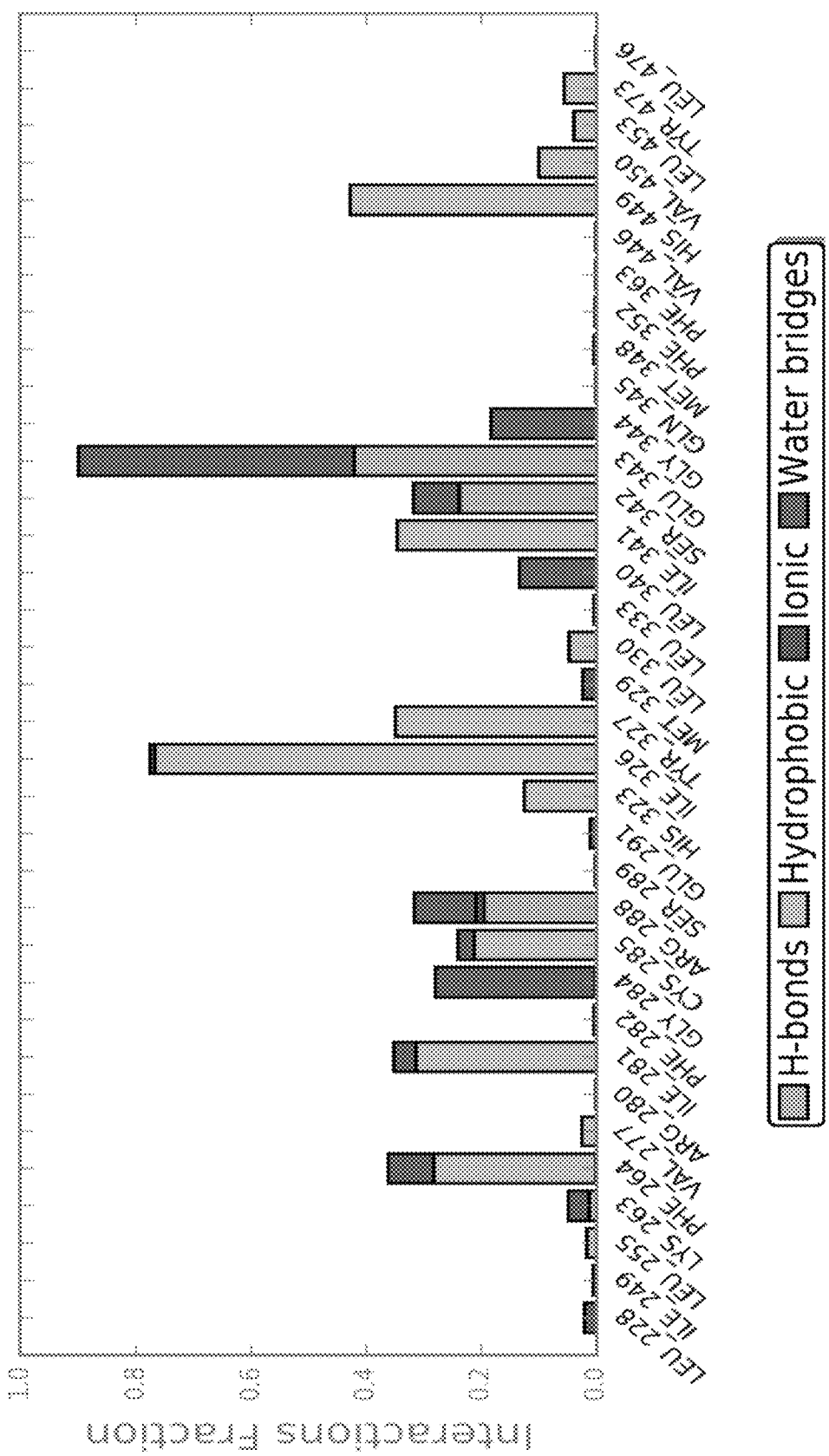
FIG. 8 is a plot of interactions between compound AU9-6 and protein PPARγ throughout an MD simulation. Protein-ligand interactions (or 'contacts') are categorized into four types: Hydrogen Bonds, Hydrophobic, Ionic and Water Bridges. The stacked bar charts are normalized over the course of the 100 ns MD trajectory.
Figure 9:
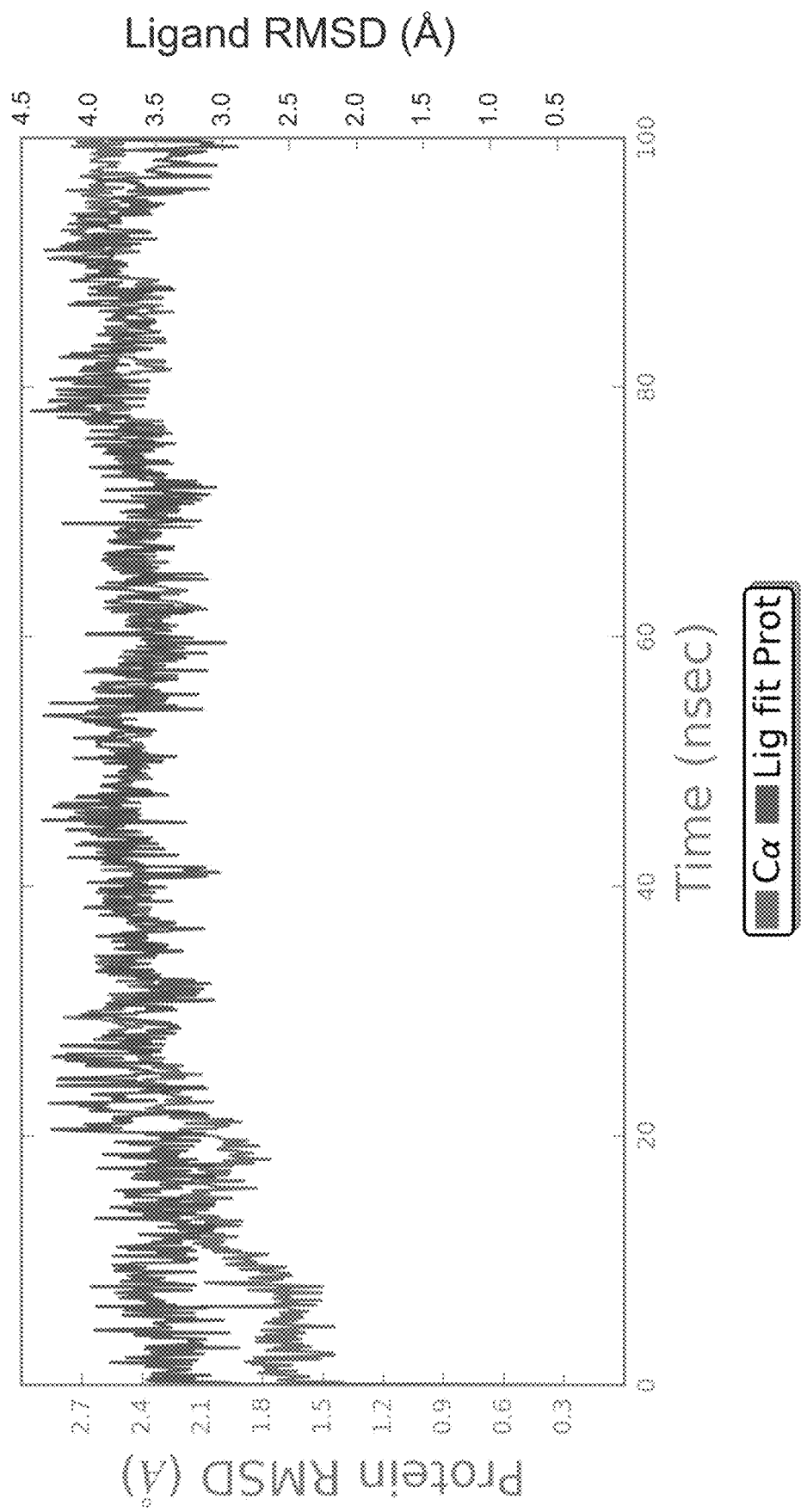
FIG. 9 is a plot of Protein-Ligand root-mean-square deviation (RMSD) for compound AU9-6 and PPARγ as a function of MD simulation time. All protein frames are first aligned on the reference frame backbone, and then the RMSD is calculated based on the atom selection (left y-axis). Ligand RMSD (right Y-axis) indicates how stable the ligand is with respect to the protein and its binding pocket.
Figure 10:
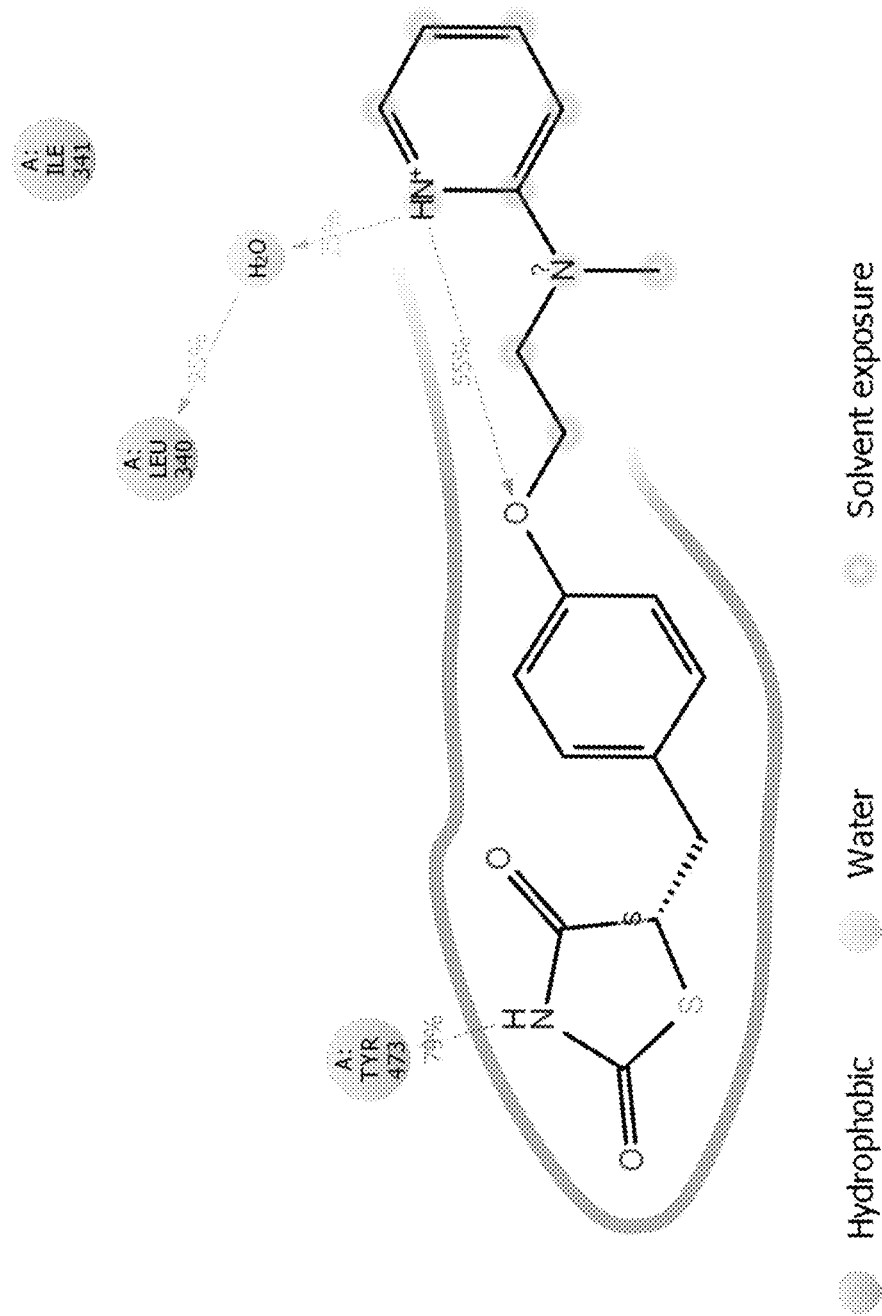
FIG. 10 is a schematic of detailed ligand atom interactions for rosiglitazone with the PPARγ residues, derived from a 100 ns molecular dynamics (MD) simulation. Interactions that occur more than 24.0% of the simulation time in the selected trajectory (0.00 through 100.00 nsec), are shown.
Figure 11:
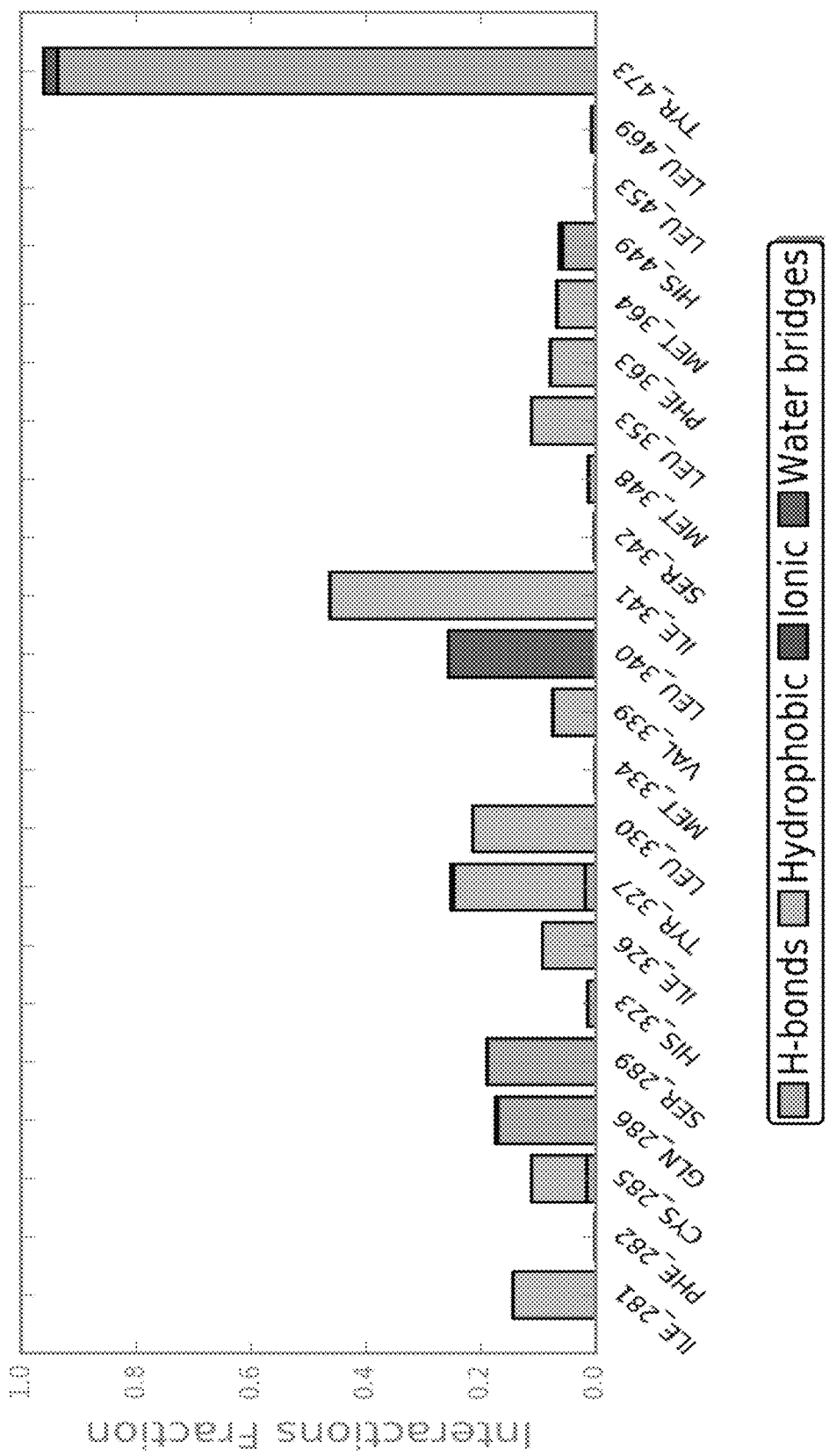
FIG. 11 is a plot of interactions between rosiglitazone and protein PPARγ throughout an MD simulation. Protein-ligand interactions (or 'contacts') are categorized into four types: Hydrogen Bonds, Hydrophobic, Ionic and Water Bridges. The stacked bar charts are normalized over the course of the 100 ns MD trajectory.
Figure 12:
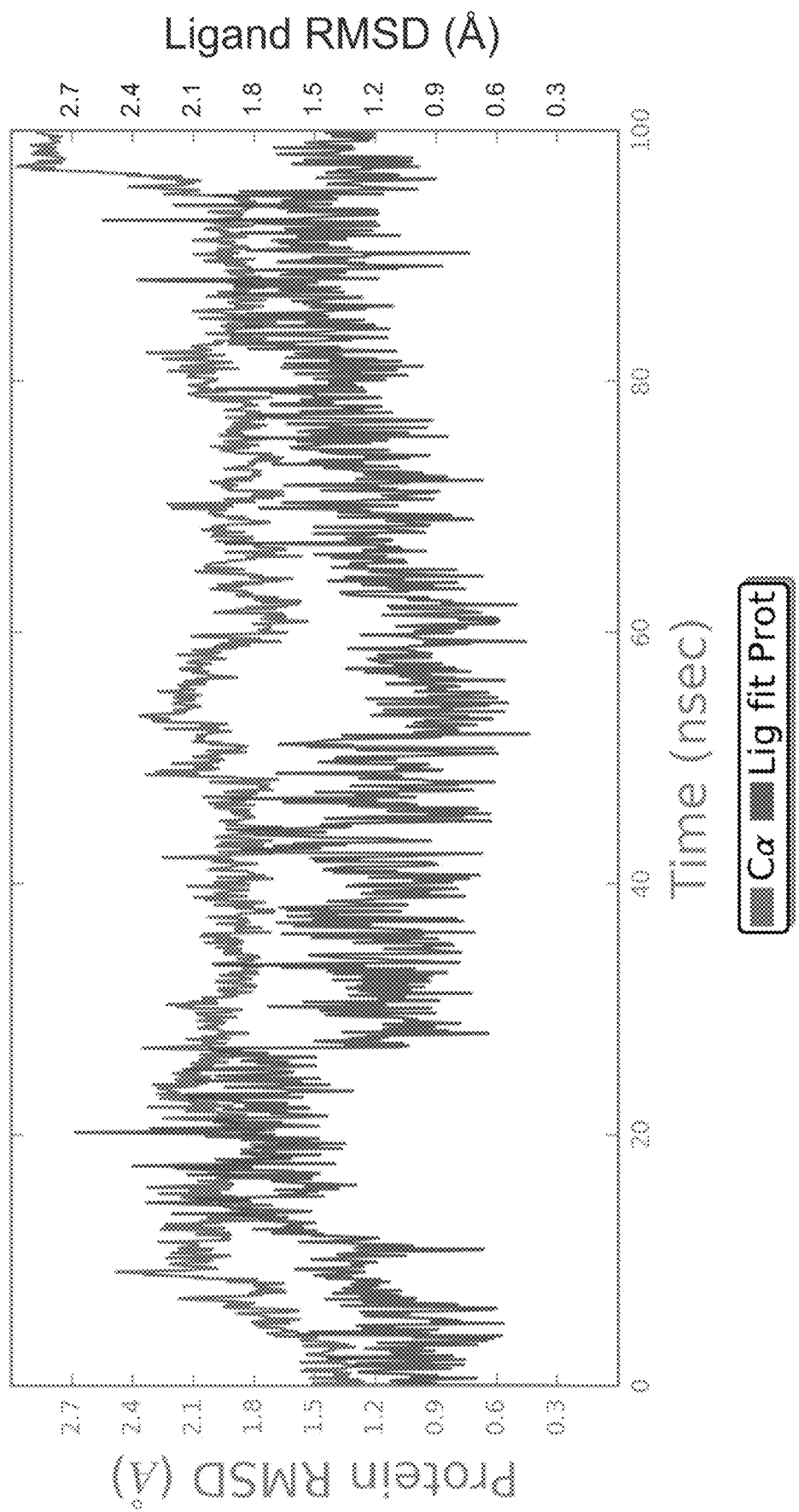
FIG. 12 is a plot of Protein-Ligand root-mean-square deviation (RMSD) for rosiglitazone and PPARγ as a function of MD simulation time. All protein frames are first aligned on the reference frame backbone, and then the RMSD is calculated based on the atom selection (left y-axis). Ligand RMSD (right Y-axis) indicates how stable the ligand is with respect to the protein and its binding pocket.
Figure 13:
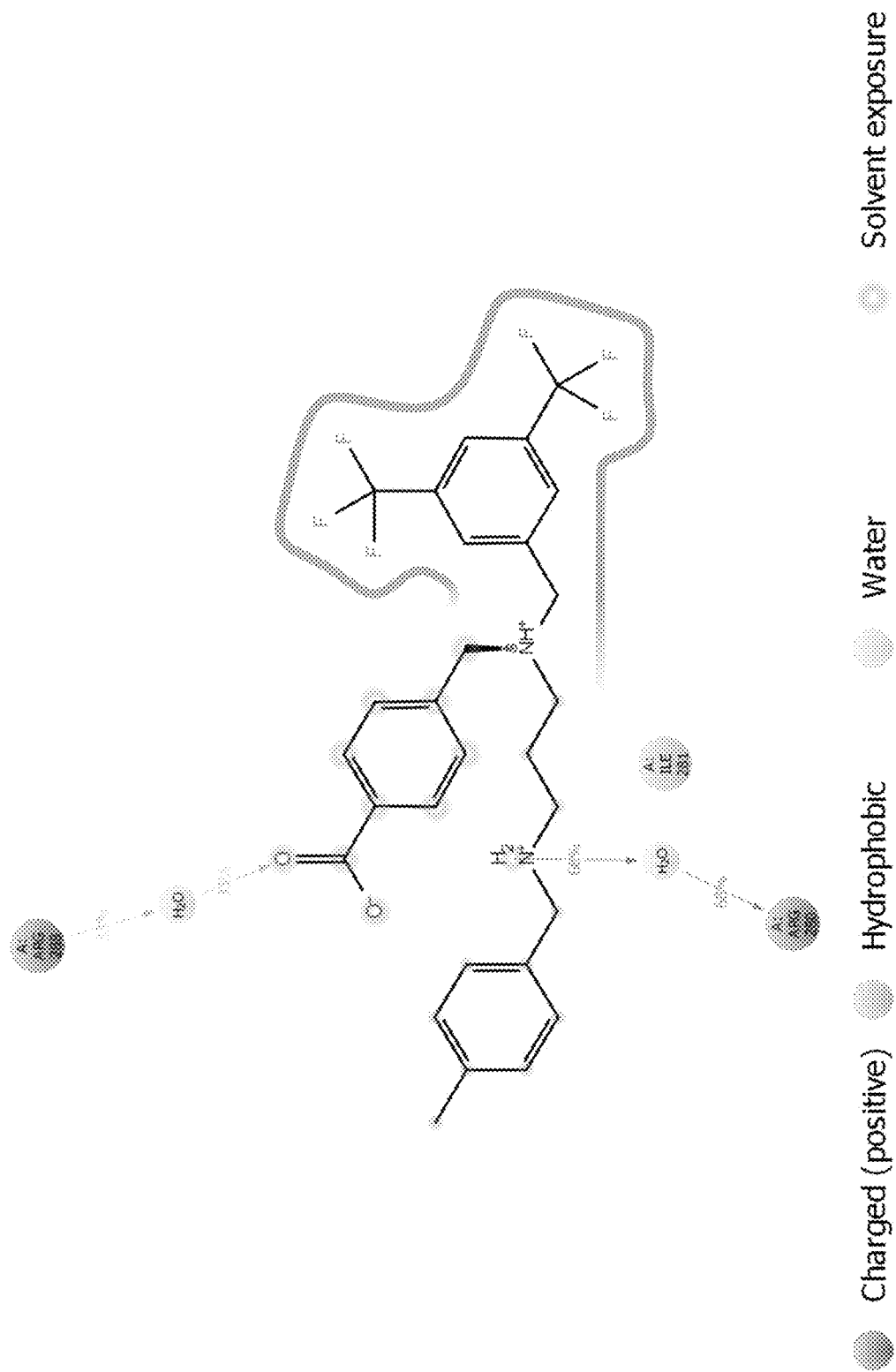
FIG. 13 is a schematic of detailed ligand atom interactions for compound 9 with the PPARγ residues, derived from a 100 ns molecular dynamics (MD) simulation. Interactions that occur more than 30.0% of the simulation time in the selected trajectory (0.00 through 100.00 nsec), are shown.
Figure 14:
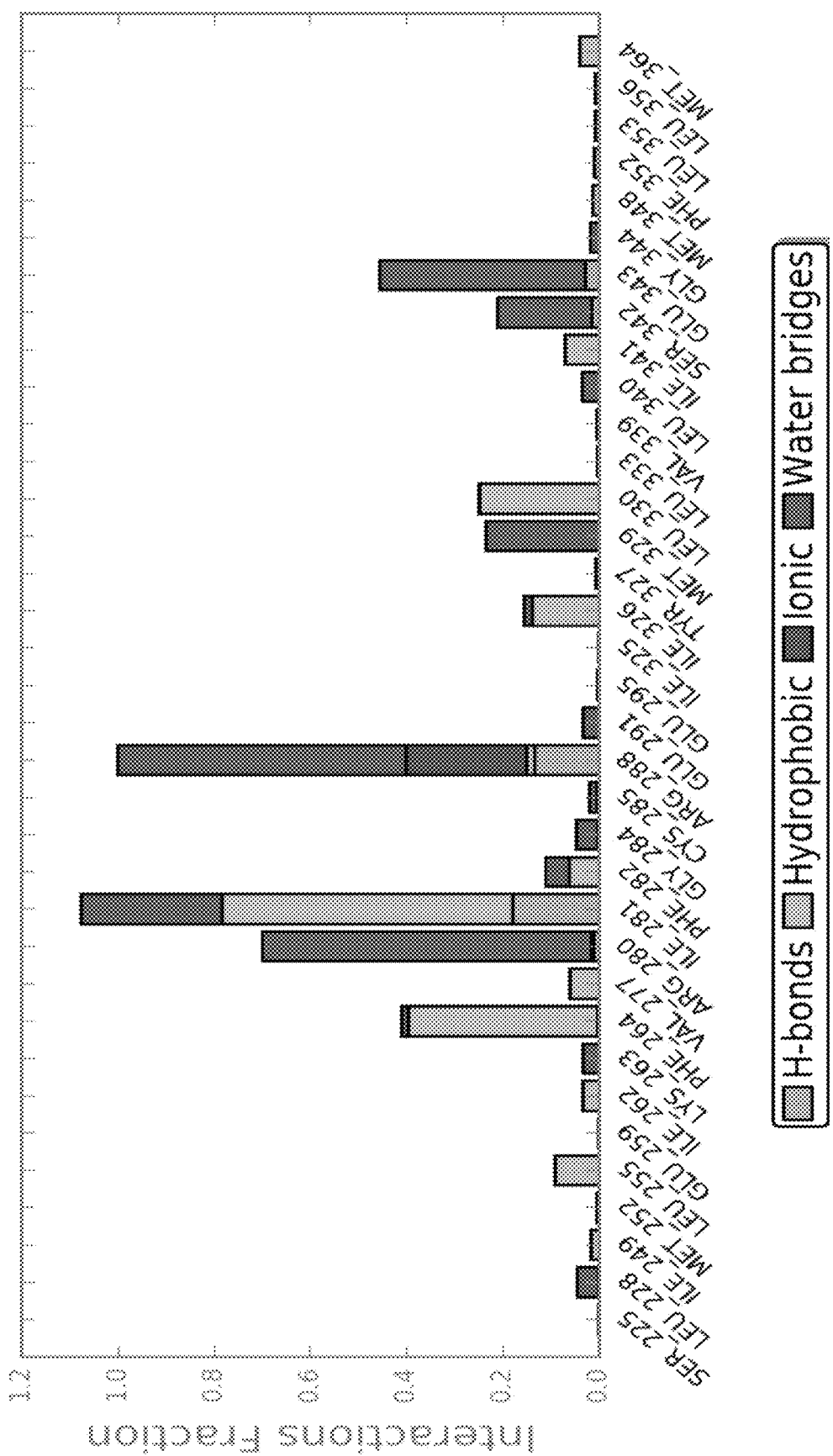
FIG. 14 is a plot of interactions between compound 9 and protein PPARγ throughout an MD simulation. Protein-ligand interactions (or 'contacts') are categorized into four types: Hydrogen Bonds, Hydrophobic, Ionic and Water Bridges. The stacked bar charts are normalized over the course of the 100 ns MD trajectory.
Figure 15:
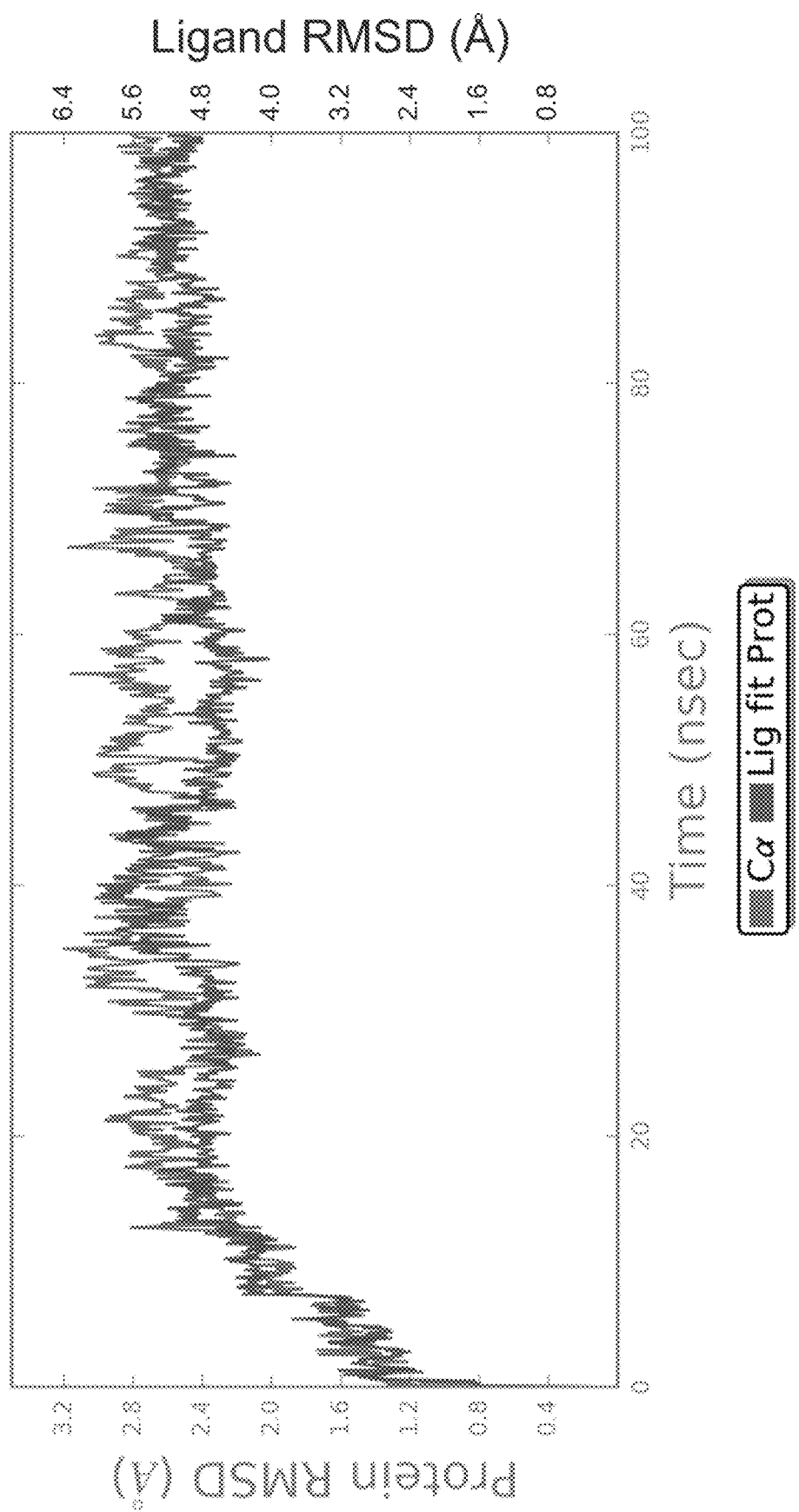
FIG. 15 is a plot of Protein-Ligand root-mean-square deviation (RMSD) for compound 9 and PPARγ as a function of MD simulation time. All protein frames are first aligned on the reference frame backbone, and then the RMSD is calculated based on the atom selection (left y-axis). Ligand RMSD (right Y-axis) indicates how stable the ligand is with respect to the protein and its binding pocket.

The inventive compounds do not exhibit this undesired interaction between ligand and Tyr473 (FIG. 1 to FIG. 9). MD simulations of the inventive compounds demonstrate little or no interaction with this residue (FIG. 2, FIG. 5, and FIG. 8). Similarly, the PPAR-γ activity assay (FIG. 17) shows that mutation of Tyr473 to Ala does not have a major effect on the activity of the inventive compounds.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound having the following structure:

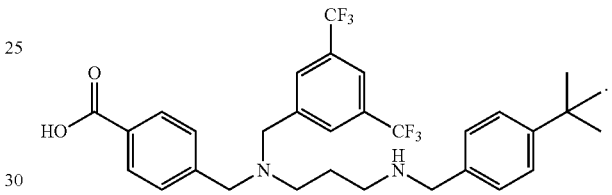

2. A composition comprising a compound of claim 1.

3. The composition of claim 2, wherein the composition further comprises an additional therapeutic.

* * * * *